United States Patent
Baker et al.

(10) Patent No.: US 6,414,202 B1
(45) Date of Patent: Jul. 2, 2002

(54) MEMBRANE-AUGMENTED MANUFACTURE OF PROPYLENE DERIVATIVES

(75) Inventors: Richard W. Baker; Andre R. Da Costa, both of Palo Alto; Ramin Daniels, San Jose, all of CA (US)

(73) Assignee: Membrane Technology and Research, Inc., Menlo Park, CA (US)

( * ) Notice: Subject to any disclaimer, the term of this patent is extended or adjusted under 35 U.S.C. 154(b) by 0 days.

(21) Appl. No.: 09/651,483

(22) Filed: Aug. 30, 2000

(51) Int. Cl.[7] ............................................... C07C 29/04
(52) U.S. Cl. ....................................... 568/895; 568/896
(58) Field of Search .................................. 568/895, 896

(56) References Cited

U.S. PATENT DOCUMENTS

| | | | |
|---|---|---|---|
| 3,758,603 A | 9/1973 | Steiglemann et al. | 260/677 A |
| 4,623,704 A | 11/1986 | Dembicki et al. | 526/68 |
| 4,701,187 A | 10/1987 | Choe et al. | 55/16 |
| 4,910,276 A | 3/1990 | Nakamura et al. | 526/247 |
| 5,488,185 A * | 1/1996 | Ramachandran et al. | 568/896 |
| 5,670,051 A | 9/1997 | Pinnau et al. | 210/651 |
| 5,710,345 A | 1/1998 | Navarrini et al. | 568/596 |
| 5,769,927 A | 6/1998 | Gottschlich et al. | 95/39 |

OTHER PUBLICATIONS

C. Staudt–Bickel et al., "Olefin/paraffin gas separations with 6FDA–based polyimide membranes", J. Membrane Science 170, 205–214, 2000.

S. Ando et al., "Perfluorinated polymers for Optical Waveguides", Chemtech, p.20–27, Dec. 1994.

R. Hughes et al., "Olefin Separation by Facilitated Transport Membranes", in *Recent Developments in Separation Science*, N. Li et al. (eds)., CRC Press, Boca Raton, FL. (1986).

* cited by examiner

*Primary Examiner*—Sreeni Padmanabhan
(74) *Attorney, Agent, or Firm*—J. Farrant

(57) ABSTRACT

A process for manufacturing isopropyl alcohol by reacting propylene with a reagent, including treating a vent stream from the reaction zone, to recover propylene for return to the reactor. The process involves using a gas separation membrane to separate propylene from propane in the reactor vent stream. The membrane separation step results in a residue stream typically containing as much as 30% propane or more, which is vented from the process, and a permeate stream typically containing 95% or less propylene, which is recirculated to the reactor.

16 Claims, 8 Drawing Sheets

MEMBRANE-AUGMENTED MANUFACTURE OF PROPYLENE DERIVATIVES

FIELD OF THE INVENTION

The invention concerns manufacturing of propylene derivatives. More specifically, the invention concerns the selective purging of propane and recovery of propylene in the process by using gas separation membranes to treat the reactor vent stream.

BACKGROUND OF THE INVENTION

The United States produces more than 10 billion pounds annually of chemicals derived from propylene. Important derivatives include acrylonitrile, butyl alcohol, propylene oxide, isopropyl alcohol and cumene.

In a typical propylene derivative manufacturing process, propylene and other reagents are introduced into a high-pressure reactor. The raw effluent from the reactor is transferred continuously to one or more separation steps, from which a stream of raw derivative product is withdrawn for further purification. A stream of overhead gases, containing unreacted propylene, is also withdrawn from the separation steps. If the conversion of propylene to product is high, such as 95% or above, these overhead light gases may simply be sent to the fuel line. In many cases, however, propylene conversion per pass is much lower than this, and the overhead gas is recirculated to the reactor. Thus, the propylene feed to the reactor is a combination of fresh propylene and propylene recirculated in the reactor/product separation process loop. The fresh feed is usually chemical-grade propylene, a high-purity reagent that has a propylene content of about 95% or above, the remaining 5% or less being mostly propane, which passes unchanged through the reactor. Although the proportion of inert gas introduced into the reactor loop with the fresh feed in this way is small, the amount circulating builds up quickly, reducing the catalyst activity and reactor productivity. Propane build-up is usually controlled to a steady-state propane content in the loop in the range about 5–30%, by continuously venting a small fraction of the overhead gas from the recirculation loop.

Such a purge operation is unselective however, and, since the vent stream may contain as much as 90 vol % or more of propylene, multiple volumes of propylene may be lost from the loop for every volume of propane that is purged. Even though the volume of gas vented is only a few percent of the volume of fresh feed, the propylene lost in this way may typically amount to a few million pounds per plant per year, with a value of $1 million or more.

Despite its high value, propylene recovery from the purge stream, by separating it from the propane before the propane is vented, is generally not cost effective. Separation of propylene from propane is difficult, because of the similar physical properties, including close boiling points (propylene, $-48°$ C. and propane $-42.2°$ C.). When high-purity propylene is manufactured, it is separated from propane in a $C_3$ splitter, a large cryogenic distillation column that typically contains 150 or more trays. It is clearly not practical or economic to install such equipment solely for purge treatment. Pressure swing adsorption (PSA), which can make product streams of high purity, has also been considered, but available adsorbents are not very effective, and PSA systems are also costly and energy intensive.

In summary, the concentration of propane in the reactor is regulated by the rate of purging via the vent stream; to achieve maximum productivity from the reactor and a high conversion of propylene to product, the propylene concentration in the reactor should be as high, and the propane content as low, as possible. Without the ability to recover propylene from the purge gas, however, there is an inevitable trade-off between controlling propane concentration in the reactor and losing propylene feedstock in the purge vent stream, by which operators of polypropylene plants are constrained. By purging a chosen percentage of the effluent light overhead gas, the operator makes what is for him, in the circumstances specific to the plant, the most acceptable compromise between the two undesirable extremes of excessive propylene loss and excessive loss of reactor efficiency.

Separation of propylene from propane by means of membranes is discussed extensively in the literature. It is well known that numerous materials and membranes exist with intrinsic selectivity for propylene over propane. These include facilitated transport membranes, polymeric membranes and inorganic membranes.

Membranes are not immediately attractive, however, for propylene recovery from vent gas, because, unlike PSA and cryogenic distillation, membranes are not able to produce a high-purity propylene permeate stream and at the same time achieve high levels of propylene recovery. The reason for this is that a membrane is not a perfectly selective barrier. If the membrane area and time in which the molecules of the gas stream are in contact with the membrane surface are very small, only a very small cut of the total feed flow will permeate. Since propylene permeates faster than propane, most of this small permeate cut will be propylene. That is, the permeate stream will have high propylene purity, and the residue stream will have a composition that is not much changed from the membrane feed composition. In other words, most of the propylene that was present in the feed gas will remain on the feed side, and will be lost when that gas is vented. Propylene recovery can be increased by increasing membrane area and contact time for the gas molecules. However, in this case propane permeation will also be increased. In other words, increasing propylene recovery also results in increasing propane recovery. Thus, little propylene will remain on the feed side to be lost by venting, but the recovered gas will be of low propylene purity.

Furthermore, the propylene/propane selectivity that can be obtained from most membranes under real operating conditions is small. Although literature references cite propylene/propane selectivities even as high as 50 or more, these data have generally been obtained from experiments with pure gases under low feed pressure conditions and with a vacuum on the permeate side of the membrane. With gas mixtures at high pressures, the best propylene/propane selectivity that can be obtained is typically no higher than between 2 and 3.

Despite these inherent difficulties, it has been proposed to apply membrane separation to the recovery of light olefins from reactor vents. U.S. Pat. No. 4,623,704 describes such a process for recovering ethylene from the reactor vent of a polyethylene plant. In this case of polyethylene manufacturing, the reactor is run at very high ethylene, very low ethane levels, so that the vent stream contains 96.5% ethylene, only 2.7% ethane and smaller amounts of methane and nitrogen. The stream is passed across a cellulose triacetate membrane that is selective for ethylene over ethane. Although the membrane selectivity is poor, the membrane produces an upgraded permeate stream, now containing 97.9% ethylene and 1.5% ethane, which is considered sufficiently free of impurities for return to the reactor, and a residue stream containing 89.9% ethylene, 8.5% ethane, which is purged from the reactor loop and used as fuel gas.

A chapter by R. D. Hughes et al., entitled "Olefin Separation by Facilitated Transport Membranes", in *Recent*

*Developments in Separation Science,* N. N. Li et al. (Eds), CRC Press, 1986, discusses pilot-scale tests of a facilitated-transport membrane module at a polypropylene plant. The module was used to treat vent gas from the reactor with a view to recovering propylene. The test was a technical success for the membranes, in that the module was able to produce a permeate stream typically containing about 97–99% propylene. However, since the membrane process could not produce polymer-grade propylene, the permeate was not recirculated to the reactor, and the process was not pursued.

Thus, recovery of propylene from the propane vent stream of reactors using propylene as a feedstock has been recognized to be desirable for many years. It has also been recognized that the recovered propylene needs to be of comparably high purity to the fresh reactor feedstock if it is to be recirculated in the process. Although methods for separating propylene from a propylene/propane mixture exist, they are impractical for vent stream treatment, either because they are too costly, or because they cannot produce propylene of sufficient purity.

SUMMARY OF THE INVENTION

The invention is an improved process for making propylene derivatives, specifically, but not exclusively: cumene; chlorohydrin, a precursor of propylene oxide; isopropyl alcohol; and butyraldehyde, a precursor of butyl alcohol. The process involves carrying out a reaction of propylene with the appropriate reagent or reagents in a reactor, separating the derivative product from the reactor effluent, and recirculating unreacted propylene to the reactor. The process includes a membrane separation step to provide selective purging of propane and other inert components from the reactor loop, and to recover a propylene-enriched stream for return to the reactor. In a basic aspect, the process of the invention comprises the following steps:

(a) carrying out one of the following reaction steps in a reaction zone:
 (i) the reaction of propylene with hypochlorous acid wherein the propylene derivative chlorohydrin is made;
 (ii) the reaction of propylene with water wherein the propylene derivative isopropyl alcohol is made;
 (iii) the reaction of propylene with carbon monoxide and hydrogen wherein the propylene derivative butyraldehyde is made;
 (iv) the reaction of propylene with benzene wherein the propylene derivative cumene is made;

(b) withdrawing from the reaction zone an effluent comprising propylene, propane and the propylene derivative;

(c) subjecting the effluent to at least one separation step, thereby producing a raw propylene derivative stream and a gas stream;

(d) passing at least a portion of the gas stream across a feed side of a membrane selective for propylene over propane;

(e) withdrawing from a permeate side of the membrane a permeate stream enriched in propylene compared to the gas stream;

(f) withdrawing from the feed side a residue stream enriched in propane compared to the gas stream;

(g) recirculating at least a portion of the permeate stream to the reaction zone.

The reaction and separation steps (a) through (c) are carried out as generally taught in the prior art. The reaction itself may take place in the gas phase or the liquid phase, using such reagents, catalysts, solvents and other additives as are known and available. Specific reagents and reaction schemes to make the particular propylene derivatives are discussed in more detail below.

The separation step that creates the crude propylene derivative product stream and the propylene-containing gas stream may be carried out in any convenient manner, such as by flashing, cooling/condensation, distillation, absorption or combinations of these, depending on whether the effluent from the reactor is in the liquid phase or the gas phase, and on what other components are present.

The membrane separation steps (d) through (f) may be carried out on the entirety of the stream to be recirculated to the reactor, or on a part of the stream, with the other part of the stream being recirculated directly to the reactor. In processes where the propylene conversion per pass is high and the propylene concentration in the fresh feed is high, the volume flow rate of overhead gas to be treated is comparatively small, and it is often cost-effective to treat the entire stream. In processes where the propylene conversion per pass is relatively low, and/or the propylene concentration in the fresh feed is low, the volume flow rate of overhead gas to be treated is comparatively large, and it will frequently be impractical to treat more than a portion of the stream.

The membrane separation steps may take the form of a single membrane separation operation or of multiple sub-operations, depending on the feed composition, membrane properties and desired results.

The membrane feed stream typically contains more than 5% propane and less than 95% propylene. The membrane separation steps produce a residue stream with a relatively high concentration of propane, such as as much as 30%, 40% or more, which is vented from the reactor loop. In this way, the amount of propylene vented from the process is reduced, compared with prior art unselective purging. Typically, the amount of propylene lost with the vented propane may be reduced from, for example, four volumes of propylene per volume of propane to one or two volumes of propylene per volume of propane. The amount of propylene removed can be controlled by varying the stage-cut at which the membrane unit operates, as explained in the Detailed Description below.

The membrane separation steps also produce a permeate stream enriched in propylene compared with the membrane feed stream, but not of high propylene purity. The higher the propylene recovery, the less enriched in propylene will be the permeate stream. Thus, the membrane permeate stream typically has a propylene concentration that is below 95% or below 90%. This stream is recirculated directly or indirectly to the reaction zone.

As mentioned, the membrane permeate stream usually comprises only part of the recirculated gas, the other part being gas that is recirculated directly in the loop without passing through membrane treatment. However, the propylene content of the recirculated membrane permeate stream is increased at least slightly compared with the untreated gas. Therefore, when the present process is compared with processes in which none of the recirculated gas has been treated by membrane separation, the recirculated gas has a slightly higher propylene concentration than in the comparative case. Thus, the process can provide a slightly higher propylene partial pressure and correspondingly lower propane partial pressure in the reactor than was achieved previously. This is beneficial in increasing catalyst life and efficient use of reactor capacity.

Additional separation steps may be carried out in the loop as desired to supplement the crude product separation or membrane separation steps or to remove secondary components from the stream.

The process of the invention may also be found to be useful from time to time for the manufacture of other propylene derivatives than those specified above, by following essentially the same set of process steps, namely reaction, separation of raw product from light gases, treatment of the light gases to separate propylene from propane, and recirculation of the recovered, but not highly purified, propylene to the reaction zone.

In another aspect, the invention is reactor apparatus comprising a reactor loop incorporating the reactor itself, the product separation equipment and the membrane separation unit containing a propylene-selective membrane.

It is to be understood that the above summary and the following detailed description are intended to explain and illustrate the invention without restricting its scope.

DETAILED DESCRIPTION OF THE INVENTION

The terms gas and vapor are used interchangeably herein.

The term $C_{2+}$ hydrocarbon means a hydrocarbon having at least two carbon atoms; the term $C_{3+}$ hydrocarbon means a hydrocarbon having at least three carbon atoms; and so on.

The term stage-cut as used herein means the ratio of the membrane permeate volume flow to the membrane feed volume flow.

The invention is an improved process for making propylene derivatives, particularly cumene; chlorohydrin, a precursor of propylene oxide; isopropyl alcohol; and butyraldehyde, a precursor of butyl alcohol.

The process involves carrying out a reaction of propylene with the appropriate reagent or reagents in a reactor, separating the derivative product from the reactor effluent, and recirculating unreacted propylene to the reactor.

The process provides selective purging of propane from the reactor loop. By a reactor loop, we mean a configuration in which at least a part of the effluent stream from the reactor is recirculated to the reactor. The process can be applied to any propylene derivative manufacturing loop in which propylene is fed to the reactor, and in which propylene and propane are present in the effluent from the reactor. The primary goals of the process are to remove propane from the reactor loop while controlling loss of propylene, and to return the recovered propylene for reuse in the process.

Figure 1:
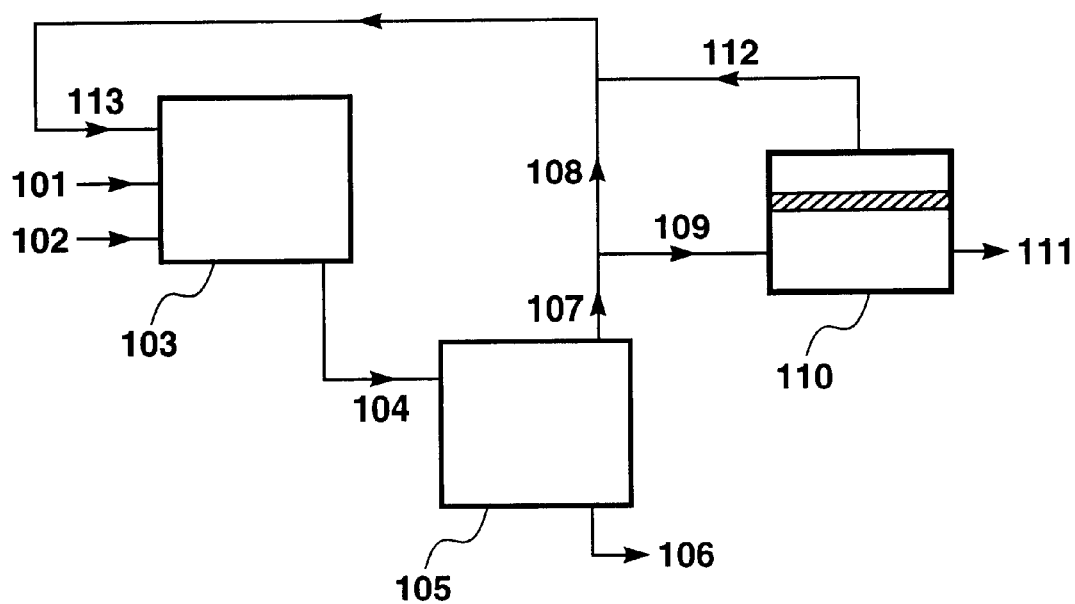
FIG. 1 is a schematic drawing showing a basic embodiment of the invention.

The invention in a basic representative embodiment is shown schematically in FIG. 1. This is an embodiment in which a portion of the light gas fraction from the reactor is recirculated without treatment, and another portion is subjected to membrane separation treatment. An alternative embodiment in which all of the overhead gas is treated is discussed later with respect to FIG. 2. It will be appreciated by those of skill in the art that these, and the other figures, are very simple block diagrams, intended to make clear the key unit operations of the process of the invention, and that an actual process train will usually include many additional components of a standard type, such as heaters, chillers, condensers, pumps, blowers, other types of separation and/or fractionation equipment, valves, switches, controllers, pressure-, temperature-, level- and flow-measuring devices and the like. It will also be appreciated by those of skill in the art that the details of the unit operations differ from product to product, as explained with respect to the individual cases below.

Referring to FIG. 1, box 103 represents the reaction step, carried out in a reaction zone using one or more reactors. The figure shows three feed streams entering the reaction zone. Stream 101 is the fresh propylene stream. This is typically, but not necessarily, chemical-grade propylene with a propylene content of about 95% or above. Stream 102 represents the feed of other reagent or reagents, the specific reagents depending on which derivative is to be made. Other materials may also be introduced into the reactor in a fluid stream if required, including catalyst, stabilizers, inhibitors or the like. Stream 113 is the stream of recirculated propylene. Commonly, the feed streams are passed through compressors and heat exchangers (not shown for simplicity) to bring them to the appropriate reaction conditions before entering the reactors. The streams can be prepared and fed separately to the reactor, or can be combined before entering the reactor.

For performing the reaction step, 103, the reactor or reactors themselves may be of any kind that provides for good contact between feedstocks and catalyst, and for good temperature control and removal of waste heat, such as shell-and-tube reactors, stirred tank reactors, and fluidized bed reactors. One or multiple reactors may be involved in the process, with the individual reactors carrying out the same or different unit operations. The exact composition of the reaction mixture may be varied in conjunction with pressure, temperature and flow rate to provide a desired overall yield, efficiency per pass and so on, as is known in the art.

If the propylene derivative being made is cumene, the reaction step 103 may be performed in the vapor or liquid phases. In a typical production process, propylene, stream 101, benzene, stream 102, and a suitable catalyst, such as phosphoric acid (vapor-phase process) or sulfuric acid (liquid-phase process), are introduced into a reactor in the reaction zone. In the preferred vapor-phase process, the reaction conditions are in the pressure range 200–500 psia and the temperature range 200–250° C. The preferred benzene:propylene molar ratio is approximately 5:1, under which conditions a propylene conversion of at least about 94%, and often higher, can be achieved. For cumene production, the fresh propylene feedstock, stream 101, is frequently of only refinery grade, that it, containing as much as about 60% propane, but may be of higher grade, such as chemical grade (about 95% propylene or above) or even polymer-grade (99+%).

Alternatively, the reaction step 103 can be carried out in the liquid-phase. In this case, the reactor temperature is typically only about 35–70° C. and the pressure is usually in the range 75–225 psia. The benzene:propylene molar ratio is approximately 6:1, and the process achieves a very high propylene conversion of about 98–99%.

If the propylene derivative being made is isopropyl alcohol, the reaction step 103 may again be performed in the liquid or the vapor phase. Water, stream 102, and chemical-grade propylene, or at least propylene of purity preferably greater than 90%, stream 101, are used as reagents, usually in a mole ratio between about 0.3:1 and 0.5:1. In the liquid-phase process, the reagents are heated to up to about 190° C. and passed into the reaction zone, which is maintained at high pressure, such as 450 psia or above. The partially liquid mixture flows over a packed bed of sulfonated ion-exchange resin and is withdrawn from the bottom of the reactor. In the alternative, the reaction step 103 is carried out by passing the same reagents into a reactor in the vapor phase, and a phosphoric acid catalyst is used instead of the ion-exchange resin.

If the desired propylene derivative product is either propylene oxide or butanol, the overall production processes are a little different from those described above, in that the process outlined in FIG. 1 results in an intermediate derivative, which is then passed to a downstream reactor or reactors for manufacture of the final product.

In the case of propylene oxide, the intermediate derivative produced in the reaction step 103 is chlorohydrin. Chlorine and water are passed in at the bottom of the reactor as stream 102 and form hypochlorous acid. Propylene, stream 101, is passed into the reactor column about half way up, and reacts with the hypochlorous acid to form chlorohydrin. In this case, the separation step 105 also takes place within the reactor column itself under gravity, as the chlorohydrin solution falls to 2) the bottom of the reactor and is removed thence as stream 106, and the gases rise to the top of the column and are withdrawn as an effluent gas stream 107. To complete the preparation of propylene oxide, chlorohydrin stream 106 is passed to a downstream reactor, not shown in FIG. 1, where it is hydrolyzed by reaction with calcium hydroxide to form propylene oxide according to the reaction:

$$2CH_2ClCH(OH)CH_3 + CA(OH)_2 \rightarrow 2CH_3CHOCH_2 + 2H_2O.$$

In the case of butanol, the product is made by oxo synthesis, that is, the hydroformylation of propylene by reaction with synthesis gas. The process results in production of both n-butanol and isobutanol. Propylene, stream 101, and synthesis gas (carbon monoxide and hydrogen) stream 102, and a dissolved rhodium-based or cobalt-based catalyst (not shown), are passed into the bottom of a reactor. The reaction zone is maintained at high temperature, up to 180° C. and high pressure, up to 3,000 psia or more. The reaction steps 103 that take place under these conditions form a mix of aldehydes and butyl alcohols. Butyraldehyde from the mixture is subsequently hydrogenated in a downstream reactor, not shown in FIG. 1, to form n-butanol and isobutanol, which can be distilled into separate products.

It will be apparent to those of skill in the art that the above are general descriptions of preferred reaction techniques that are well known. More information about these and other specific arrangements for making the various propylene derivatives is available in petrochemical engineering reference books, for example, *Handbook of Petrochemicals and Processes*, G. M. Wells, Gower Publishing, 1995; *Ullman's Encyclopedia of Industrial Chemistry*, 5th edition, Wolfgang Gerhartz, Ed., VCH Publishers, 1985; and *Chemical Processing Handbook*, J. J. McKetta (Ed.), Marcel Dekker, 1993.

It will further be apparent that the reaction step operating conditions and functioning are not critical to the invention and can and will vary from plant to plant. Thus, the scope of the invention embraces all reaction types and operating conditions consistent with producing a propylene/propane purge stream amenable to membrane separation treatment as set forth below.

The effluent stream, 104, is withdrawn from the reaction zone. Depending upon the conditions in the reactor and/or the exit conditions, this stream may be in the form of gas, liquid or a multiphase mixture. Stream 104 is introduced into a separation step, or frequently, a train of separation steps, indicated simply as box 105 in FIG. 1. The purpose of this step or steps is to separate the effluent into at least a stream, 106, containing the crude propylene derivative, and a stream, 107, containing unreacted propylene for recirculation.

Techniques that may be used in step 105 to treat the reactor effluent include flashing, cooling/condensation, distillation, absorption or combinations of these, depending on whether the effluent from the reactor is in the liquid phase or the gas phase, and on what other components are present. Physical phase separation, such as of powder or particle streams from gas streams, or of liquid streams from gas streams, can be carried out in simple gravity separators, cyclone separators or any other convenient type. All of these techniques and pieces of equipment are familiar and readily available.

If the propylene derivative being made is cumene, the reactor effluent, 104, typically passes first to a depropanizer column, as is well known in the art. Propane and unreacted propylene are removed as overhead stream 107 from this column. The remaining effluent then passes to another column where unreacted benzene is fractioned from the raw cumene product for recirculation to the reactor. The remaining raw cumene stream, 106, is sent for final purification, usually by distillation. Thus, in this case, step 105 preferably involves at least two fractionation operations, the first to remove $C_{3-}$ hydrocarbons, the second to recover benzene.

If the propylene derivative being made is isopropyl alcohol, the aqueous reactor effluent, 104, is usually cooled and passed to one or more flash steps, achieved by letting down the pressure on the effluent. The liquid fraction from the bottom of the flash tank forms raw product stream 106, and this is typically purified downstream by distillation. The light overhead stream from the flash tank contains propylene, propane and isopropyl ether. This stream can be passed to a fractionation column from which the isopropyl ether is removed as bottom fractions and the $C_{3-}$ hydrocarbons are withdrawn as overhead stream 107. Thus, in this case, the separation step 105 preferably includes flash and fractionation sub-steps.

If the propylene derivative being made is propylene oxide, the first reaction step, 103, produces chlorohydrin. As indicated above, the separation step 105 of liquid chlorohydrin solution from overhead gases normally takes place by simple gravity separation within the reactor itself. Thus the chlorohydrin stream 106 is removed directly from the bottom of the reactor and gas stream 107 is removed from the top of the reactor.

If the propylene derivative being made is butanol, the reactions that take place in reaction step 103 typically produce a mixture of alcohols and aldehydes, as mentioned above. The effluent stream, 104, from the reactor is preferably cooled to condense the products and passed to a phase separator to yield raw liquid product stream, 106, and overhead light gases stream 107. According to this embodiment, therefore, separation step 105 preferably comprises cooling, condensation and phase-separation steps.

Stream 107 is split into two streams, 108 and 109. Stream 108 is recompressed, if need be, and recirculated in the reactor loop as shown; stream 109 is removed from the reactor loop and passes as feed to the membrane separation step.

If a purging process without membrane treatment of the vent gas were to be performed, the amount of gas purged from the loop in stream 109 (and then vented in total) would reflect the level of propane removal necessary to maintain the reactor propane concentration at a certain value. For example, if the fresh propylene feed is chemical grade, containing 5% propane, then 5 lb/h of propane enters the reactor for every 100 lb/h of feed. If the propane concentration in the recirculating gas is 25%, then to vent 5 lb/h of propane, corresponding to the incoming propane, means that the total purge stream flow rate is 20 lb/h. If conversion per reactor pass is about 50%, then stream 107 also has a flow rate of about 100 lb/h, so stream 107 would be split, so that about 20 lb/h of gas is vented as stream 109 and the remainder is returned within the process as stream 108. Thus, stream 109 would represent about 20% of stream 107.

In the process of the invention, there is more flexibility in the amount of gas removed in stream 109, as will become clear from the discussion of the membrane separation step and from the examples presented below. The relative sizes of streams 108 and 109 can be selected and adjusted as desired to provide some control of the concentrations of propane and propylene in reactor 103.

Stream 109 passes as feed stream to membrane unit 110. The membrane unit contains a membrane that exhibits a substantially higher permeability for propylene than for propane. Over time, a variety of membrane types and materials have been reported in the literature with apparently useful properties for propylene/propane separation. One group of membranes that has been extensively studied for thirty years is facilitated-transport membranes. These contain a liquid that itself contains, for example, free silver ions that react selectively and reversibly with unsaturated hydrocarbons, to selectively carry propylene across the membrane. Facilitated-transport membranes with liquid carriers of this type have never reached commercial use for any separation, owing, amongst other problems, to instability under industrial conditions and to the need to saturate the feed gas with water. Such membranes are, therefore, not recommended for use in the invention.

In recent years, membranes that make use of free carrier ions dissolved in a solid polymer solution, rather than an aqueous solution, have been developed. These membrane are taught in U.S. Pat. No. 5,670,051. The membranes remain mechanically stable up to feed pressures of at least 500 psig and can work with dry feed gases. Such membranes are not yet available commercially but can be manufactured according to the teachings of that patent and are suitable for use in the claimed process.

Yet other membranes with propylene/propane separating properties are very finely porous inorganic membranes, such as carbon membranes, that act as very fine sieves that separate on the basis of difference in molecular size. Inorganic membranes are characterized by good temperature and chemical resistance. Such membranes are available commercially for propylene/propane separation, such as from Carbon Membranes Ltd., of Arava, Israel, and are reported to provide propylene/propane selectivity of up to 12–15 and propylene flux of 180 GPU under favorable conditions.

The most preferred membranes for use in the invention, however, are polymeric membranes. The permeability of a gas or vapor through a polymer film is a product of the diffusion coefficient, D, and the Henry's law sorption coefficient, k. D is a measure of the permeant's mobility in the polymer; k is a measure of the permeant's sorption into the polymer. The diffusion coefficient tends to decrease as the molecular size of the permeant increases, because large molecules interact with more segments of the polymer chains and are thus less mobile The sorption coefficient depends, amongst other factors, on the condensability of the gas.

Depending on the nature of the polymer, either the diffusion or the sorption component of the permeability may dominate. In rigid, glassy polymer materials, the diffusion coefficient tends to be the controlling factor and the ability of molecules to permeate is very size dependent. As a result, glassy membranes tend to permeate small, low-boiling molecules, such as hydrogen and methane, faster than larger, more condensable molecules, such as $C_{2+}$ organic molecules. For rubbery or elastomeric polymers, the difference in size is much less critical, because the polymer chains can be flexed, and sorption effects generally dominate the permeability. Elastomeric materials, therefore, tend to permeate large, condensable hydrocarbon molecules faster than small, low-boiling molecules. Thus, most rubbery materials are selective in favor of all $C_{3+}$ hydrocarbons over methane. For propylene/propane separation, both the boiling points (–48° C. propylene, –42.2° C. propane) and the molecular diameters (4.0 Å for propylene, 4.3 Å for propane) are close. Thus, many polymer materials, both rubbery and glassy, have little or no selectivity for propylene over propane. However, some glassy materials are known from published experimental data to have useful separation properties, and these are the preferred materials. Examples of such polymers that can be used to make propylene/propane separating membranes are poly(phenylene oxide) (PPO), and polyimides, particularly 6FDA-based polyimides, where 6FDA is the structure:

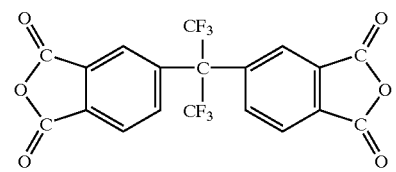

Representative 6FDA polyimides include 6FDA-ODA,

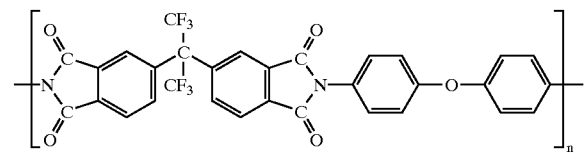

where n is a positive integer;

6FDA-NDA,

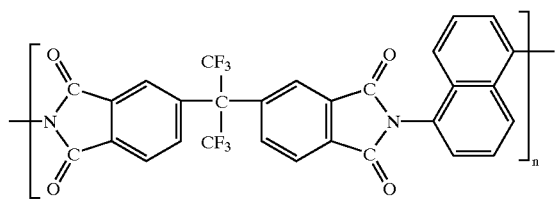

where n is a positive integer;
6FDA-TMPD,

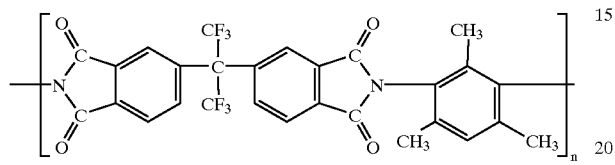

where n is a positive integer.

Between these three, 6FDA-NDA is most preferred because, as shown in the experimental examples, below, we found that composite membranes using this polymer as a selective layer exhibited the best combination of propylene flux and propylene/propane selectivity as measured with propylene/propane gas mixtures. Other 6FDA polyimides that may be used, although they have lower propylene permeability than those listed above, are 6FDA-IPDA,

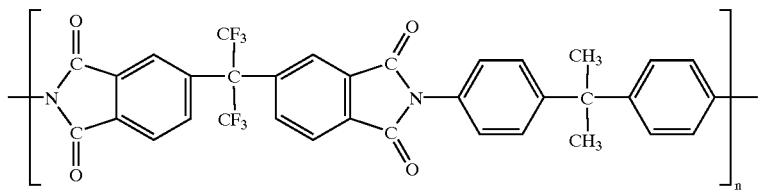

where n is a positive integer;
and 6FDA-FpDA,

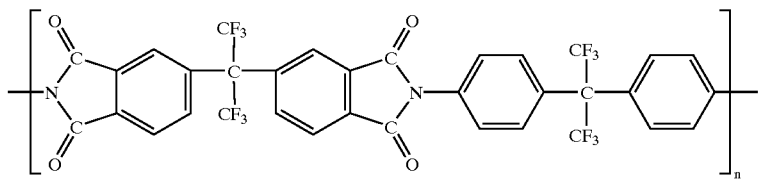

where n is a positive integer.

Permeation data for films and membranes made from these latter two polyimides are reported in C. Staudt-Bickel et al., "Olefin/paraffin gas separations with 6FDA-based polyimide membranes", *Journal of Membrane Science*, Vol. 170, pages 205–214 (2000).

Another polyimide class that is believed to contain useful selective layer materials is the perfluorinated polyimides. Such materials have been investigated for use as optical waveguides, and their preparation is described, for example, in S. Ando et al., "*Perfluorinated polymers for optical waveguides*", CHEMTECH, December, 1994. To be usable as membrane materials, the polyimides have to be capable of being formed into continuous films. Thus, polyimides that incorporate ether or other linkages that give some flexibility to the molecular structure are preferred. Particular examples are polymers comprising repeat units prepared from the perfluorinated dianhydride 1,4-bis(3,4-dicarboxytrifluorophenoxy) tetrafluorobenzene (10FEDA), which has the structure:

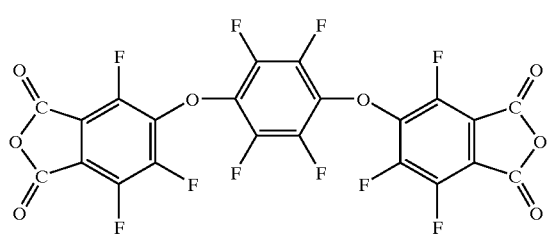

Diamines with which 10FEDA can be reacted to form polyamic acids and hence polyimides include 4FMPD, which has the structure:

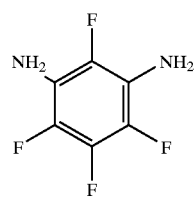

The resulting 10FEDA/4FMPD polyimide has the repeat unit structure:

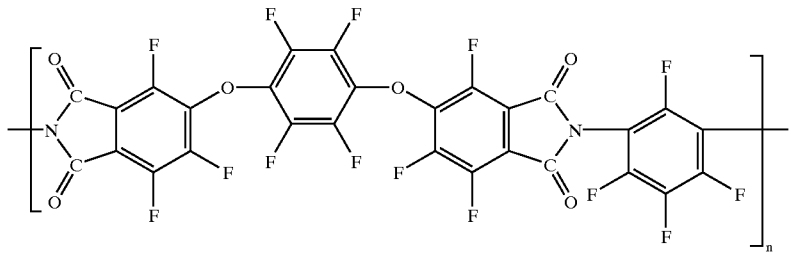

where n is a positive integer.

Yet another group of polymers that includes particularly preferred materials is glassy polymers characterized by having repeating units of a fluorinated, non-aromatic cyclic structure, the ring having at least five members, and further characterized by a fractional free volume no greater than about 0.3. Preferred polymers in this group are formed from fluorinated monomers of (i) dioxoles, which are five-member rings of the form

that polymerize by opening of the double bond, or (ii) dioxolanes, similar five-member rings but without the double bond in the main ring, or (iii) aliphatic structures having an alkyl ether group, polymerizable into cyclic ether repeat units with five or six members in the ring. The polymers may take the form of homopolymers or copolymers. Such materials are discussed at length in copending patent application Ser. No. 09/574,420 entitled "Gas Separation Using Organic-Vapor-Resistant Membranes", which is incorporated herein by reference as it relates to olefin/paraffin separations.

Specific most preferred materials in this group are copolymers of tetrafluoroethylene with 2,2,4-trifluoro-5-trifluoromethoxy-1,3-dioxole having the structure:

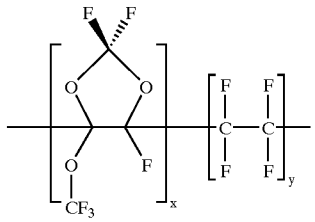

where x and y represent the relative proportions of the dioxole and the tetrafluoroethylene blocks, such that x+y=1.

Such materials are available commercially from Ausimont S.p.A., of Milan, Italy under the trade name Hyflon® AD. Different grades are available varying in proportions of the dioxole and tetrafluoroethylene units.

A second highly preferred material of this type has the structure:

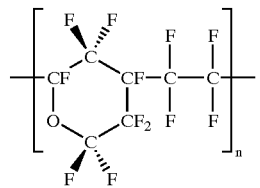

where n is a positive integer.

This material is available commercially from Asahi Glass Company, of Tokyo, Japan under the trade name Cytop®.

Because all of these preferred polymers are glassy and rigid, an unsupported film of the polymer is usable in principle as a single-layer gas separation membrane. However, such layers are normally far too thick to yield acceptable transmembrane flux, and preferably, the separation membrane comprises a very thin selective layer that forms part of a thicker structure, such as an asymmetric membrane or a composite membrane. The thin skin or coating layer is responsible for the separation properties and the underlying integral or discrete microporous support layer is responsible for mechanical strength. Additional layers can be added if desired, such as to seal the support layer before the selective layer is applied, to protect the surface from abrasion, and so on. The membranes may be manufactured as flat sheets or as fibers and housed in any convenient module form, including spiral-wound modules, plate-and-frame modules and potted hollow-fiber modules. The making of all these types of membranes and modules is well known in the art. Flat-sheet membranes in spiral-wound modules are our most preferred choice.

Since conventional polymeric materials are used for the membranes, they are relatively easy and inexpensive to prepare and to house in modules, compared with other types of membranes that might be used, such as pyrolysed carbon membranes and ceramic membranes.

To achieve a high flux of the preferentially permeating propylene, the selective layer responsible for the separation properties should be thin, preferably, but not necessarily, no thicker than 10 µm, and typically no thicker than 5 µm. It is preferred that the selective layer be sufficiently thin that the membrane provide a pressure-normalized propylene flux, as measured with pure propylene at 25° C., of at least about 10 GPU (where 1 GPU=1×10$^{-6}$ cm$^3$(STP)/cm$^2$·s·cmHg), and more preferably at least about 20 GPU.

As mentioned in the Background section above, the propylene/propane selectivity that can be obtained from most membranes under real operating conditions is small. However, as shown in the Examples section below, and contrary to what has generally been believed to be the case by those of skill in the art, useful processes are possible even with low propylene/propane selectivity. Thus the propylene/propane selectivity of the membranes when in use in the process is preferably at least about 2, and more preferably at least about 3. Higher selectivity membranes, if they are available, may be used but are not required.

A driving force for transmembrane permeation is provided by a pressure difference between the feed and permeate sides of the membrane. If the overhead gas after the crude product separation steps remains at high pressure, such as above 100 psig, then this is usually adequate to carry out the membrane separation step without additional compression. If stream 107 has been let down to low pressure, such as atmospheric or close to atmospheric, then compression, preferably to 100 psig or above, is needed to drive the membrane separation step. However, in that case, stream 108 also requires recompression before it can be returned to the reactor, so it is often possible to use one compressor for both purposes. Alternatively, if the pressure of stream 109 is inadequate for whatever reason, a compressor may be included in the line upstream of the membrane unit to specifically boost the membrane feed stream pressure as appropriate.

The membrane separation step divides the purge stream 109 into a residue vent stream, 111, enriched in propane and depleted in propylene, and a permeate stream, 112, enriched in propylene and depleted in propane.

The selective purging capability thus provided by the membrane separation step can be used to advantage in several ways. In one aspect, the relative masses of propane and propylene vented from the reactor recycle loop can be controlled by varying the stage-cut through the membrane. Stage-cut is defined as the ratio of total permeate flow to total feed flow, and is typically expressed as a percentage. For example, a stage-cut of 20% means that of 100 volumes of feed gas, 20 volumes pass to the permeate side and 80 volumes remain on the feed side. At low stage-cuts, comparatively little removal of propylene from the feed stream is achieved, and if the residue stream is vented at this point, comparatively large amounts of propylene are lost. As the stage-cut increases, a higher proportion of the propylene passes into the permeate stream, and the higher the stage-cut, the less propylene will be left in the residue stream. Thus, recapture of any amount of propylene feedstock is possible, at least theoretically, by an appropriately high choice of stage-cut. Of course, membrane area required to perform the separation scales in proportion to stage-cut, which will impose a practical limit on recovery. Also as explained above, the higher the propylene recovery, the lower the propylene concentration in the permeate stream.

As a guideline, in light of these considerations, it is preferred to operate at a stage-cut of at least about 30%, more preferably at least about 40%, and most preferably at least about 50%. Especially if stream 109 has a very high concentration of propane, even higher stage-cuts, such as up to 70% or even 80% or more may be used. The result is that the proportions of propane and propylene in the residue stream are significantly different than those in the membrane feed stream. By significantly, we mean that, preferably, the process is operated to yield a residue stream, 111, that has a propane content at least about 5% or more, such as 10%, 15% or 20%, greater than the membrane feed stream. In terms of the residue stream composition itself, it is preferred to operate the process to achieve a residue stream propane content of at least about 15% or higher, such as 20%, 25%, 30% or 40%. Most preferably, the residue stream has a propane content higher than about 40%. The residue stream, 111, is vented from the process and may be used as fuel or sent to any other destination as desired.

In another aspect, the membrane treatment can provide a lower concentration of propane in the reactor. By selectively retaining propane in the residue stream, the process results in a membrane permeate stream, 112, that is enriched in propylene content, typically by a few percent, compared with stream 109. Although the degree of propylene enrichment is usually less than 10%, and is frequently as little as about 1% or 2%, nevertheless, this leads to a slightly lower propane partial pressure and a slightly higher propylene partial pressure in the reactor than would be achieved if all of the recirculated gas capacity were to be provided by untreated gas 108. Even though the resulting change in reactor propylene and propane partial pressures is small, those of skill in the art will recognize that this is very beneficial in improving product yield and prolonging catalyst life. This important benefit is illustrated more fully in the Examples below. This issue is also discussed in more detail in co-owned U.S. Pat. No. 6,271,319 entitled "Membrane-Augmented Polypropylene Manufacturing" incorporated herein by reference.

Thus, by following the teachings herein, those of skill in the art will now be able to design and execute propylene derivative manufacturing processes that are characterized by better conversion per pass, lower propylene loss, or most importantly both better conversion and lower propylene loss together, than was previously accomplished or recognized to be possible by practitioners of the art.

Permeate stream 112 is shown in FIG. 1 as being combined directly with untreated recirculation stream 108 to form recirculation stream 113. Although the ultimate destination of the recovered propylene is the main reaction zone, it will be appreciated by those of skill in the art that a number of options exist for the method of permeate recycle. For example, it may be more efficient or convenient to return stream 112 to some point in the separation train 105, such as on the suction side of an available compressor, whence the recovered propylene can be returned as part of streams 107 and 108.

FIG. 1 shows the membrane separation step as a single box, and indeed it is preferred to carry out the membrane separation using a one-stage membrane system. However, if the first permeate stream requires further separation, it may be passed to a second bank of modules for a second-stage treatment. If the second permeate stream requires further purification, it may be passed to a third bank of modules for a third processing step, and so on. Likewise, if the residue stream requires further treatment, it may be passed to a second bank of modules for a second-step treatment, and so on. Such multistage or multistep processes, and variants thereof, will be familiar to those of skill in the art, who will appreciate that the membrane separation step may be configured in many possible ways, including single-stage, multistage, multistep, or more complicated arrays of two or more units in series or cascade arrangements.

Figure 2:
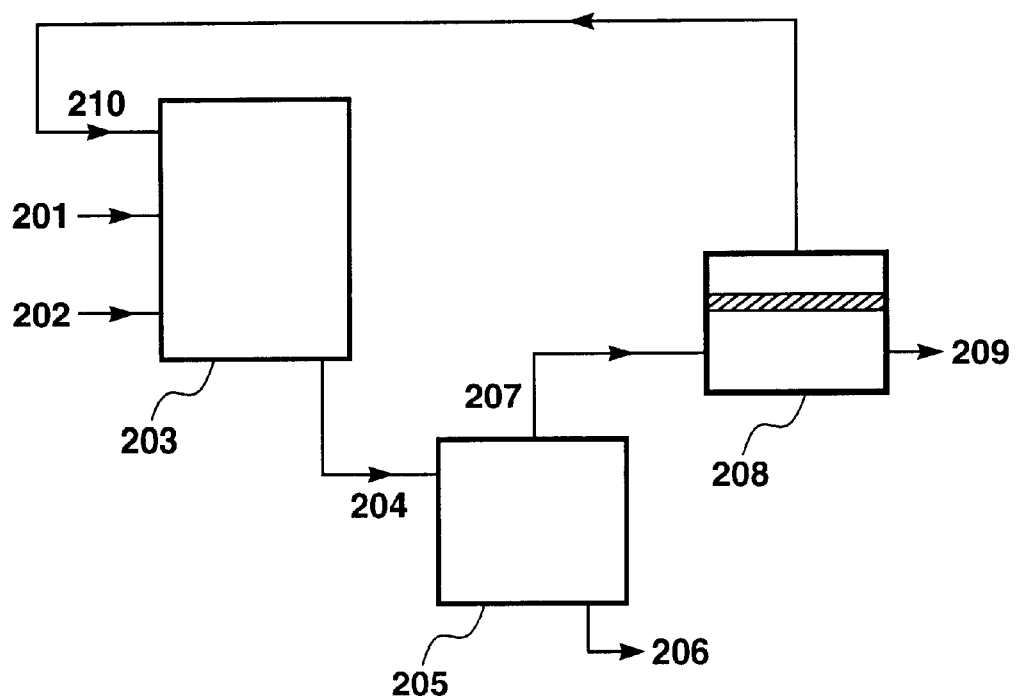
FIG. 2 is a schematic drawing showing an alternative embodiment of the invention.

FIG. 1 shows a basic embodiment in which a portion of the light gas fraction from the reactor is recirculated without treatment, and another portion is subjected to membrane separation treatment. An alternative embodiment in which all of the overhead gas is treated is shown in FIG. 2. Referring to this figure, box 203 represents the reaction step, stream 201 is the fresh propylene stream, stream 202 represents other materials introduced into the reactor as necessary, and stream 210 is the stream of recirculated propylene. As described with respect to FIG. 1, the feed streams to the reactor may be adjusted in pressure or temperature, as well as otherwise prepared in any manner desired before being introduced into the reactor.

As also described with respect to FIG. 1, the reactor may be of any type suitable for the reaction that is being carried out, and the reaction may be performed to produce an effluent stream, 204, that is a vapor, liquid or phase mixture. Stream 204 is passed into one or more separation steps, 205, to yield a raw product stream 206 and an overhead gas stream 207, containing unreacted propylene and propane. In this case, stream 207 is not split, but is sent in its entirety as feed to membrane separation step 208. Since all of the overhead gas passes through the membrane separation step in this embodiment, manufacturing processes that are characterized by a comparatively small overhead gas flow are more amenable to being carried out according to the embodiment of FIG. 2; manufacturing processes in which the overhead gas stream flow is comparatively large are more amenable to being carried out according to the embodiment of FIG. 1. By comparatively small, we mean generally having a total volume flow no more than about 500 scfm, and by comparatively large, we mean generally having a total volume flow greater than about 500 scfm. This is only a guideline, however, and if the membrane system costs are not a limiting constraint, streams of any size may be treated by the membrane unit and the overall process carried out according to the arrangement of FIG. 2.

The membrane separation step is performed using the same preferences for materials and operating conditions as described above for the FIG. 1 embodiment, to produce a residue stream, 209, that preferably has a propane content at least about 5% greater than the membrane feed stream 207. This stream is vented from the process to any desired destination. The membrane separation step also produces permeate stream 210, having a higher propylene and lower propane concentration than stream 207, which is recirculated to the reactor feed. Since all of the recirculating gas has been upgraded by the membrane separation step, this embodiment provides a total recirculation stream of higher propylene content than would be the case if overhead gas of the same flow rate and composition were handled by being split as in FIG. 1.

The invention has been described above as it relates to the manufacture of chlorohydrin, isopropyl alcohol, butyraldehyde or cumene. The process of the invention may also be found to be useful from time to time for the manufacture of other propylene derivatives than those specified above, by following essentially the same set of process steps, namely reaction with a second reagent, separation of raw product from light gases, treatment of the light gases to separate propylene from propane, and recirculation of the recovered, but not highly purified, propylene to the reaction zone. Other propylene derivatives that might be made by the process of the invention if the circumstances of their manufacture result in a light gas stream containing propylene and propane amenable to treatment by membrane separation include acrylonitrile, chemicals made by the oxo process, polygas chemicals, acrylic acid and esters, allyl chloride and epichlorohydrin. A typical manufacturing process for such a derivative will then include the following steps:

(a) carrying out in a reaction zone a reaction of propylene with a reagent to form a propylene derivative;
(b) withdrawing from the reaction zone an effluent comprising propylene, propane and the propylene derivative;
(c) subjecting the effluent to at least one separation step, thereby producing a raw propylene derivative stream and a gas stream;
(d) passing at least a portion of the gas stream across a feed side of a membrane selective for propylene over propane;
(e) withdrawing from a permeate side of the membrane a permeate stream enriched in propylene compared to the gas stream, but having a propylene concentration that is lower than about 95%;
(f) withdrawing from the feed side a residue stream enriched in propane compared to the gas stream;
(g) recirculating at least a portion of the permeate stream to the reaction zone.

The invention is now illustrated in further detail the following examples, which are intended to further clarify the invention, and are not intended to limit the scope in any way.

GROUP I EXAMPLES

Membrane Performance

Example 1

Pure-gas Permeation Data

Composite membranes with selective layers of poly (phenylene oxide) [PPO] or one of three grades of 6FDA polyimide were cut into 12.6 $cm^2$ stamps and tested in a permeation test-cell apparatus with pure oxygen, nitrogen, propane, and propylene at 25° C. feed temperature, 65 psia feed pressure, and 15 psia permeate pressure. During each test, the feed, permeate, and residue compositions were analyzed by gas chromatography (GC). The gas fluxes of the membranes were measured, and the selectivities were calculated. Table 1 summarizes the fluxes and selectivities of the composite membranes.

TABLE 1

| Membrane Selective Layer | Pressure-Normalized Flux (GPU) | | | | Selectivity (−) | |
|---|---|---|---|---|---|---|
| | $O_2$ | $N_2$ | $C_3H_6$ | $C_3H_8$ | $O_2/N_2$ | $C_3H_6/C_3H_8$ |
| PPO | 26 | 5.8 | 88.8 | 16.7 | 4.5 | 5.3 |
| 6FDA-ODA | 22 | 3.2 | 40.8 | 6.7 | 6.9 | 6.1 |
| 6FDA-TMPD | 82 | 20 | 433 | 130 | 4.1 | 3.3 |
| 6FDA-NDA | 77 | 16.4 | 50.2 | 4.0 | 4.7 | 13 |

Example 2

Mixed-Gas Permeation Data

The tests of Example 1 were repeated with a 50% propylene/50% propane gas mixture. All other test conditions were as in Example 1. The results are shown in Table 2.

TABLE 2

| Membrane Selective Layer | Pressure-Normalized Flux (GPU) | | Selectivity (−) |
|---|---|---|---|
| | $C_3H_6$ | $C_3H_8$ | $C_3H_6/C_3H_8$ |
| PPO | 34 | 7.1 | 4.8 |
| 6FDA-ODA | 6 | 2.3 | 2.6 |
| 6FDA-TMPD | 210 | 70 | 3.0 |
| 6FDA-NDA | 20 | 3.1 | 6.5 |

Example 3

Mixed-Gas Permeation Data

A composite membrane with a PPO selective layer was rolled into a spiral-wound module, which was tested in a module test apparatus at 25° C. feed temperature, 115 psia feed pressure, and 20 psia permeate pressure. The feed was a 50% propylene/50% propane gas mixture. The propylene and propane fluxes were 12 and 4 GPU, respectively, yielding a propylene/propane selectivity of 3.

As can be seen from the results of Examples 1–3, all the membrane materials tested are suitable for use in the process of the invention.

Example 4
Mixed-Gas Permeation Data

Composite membranes with selective layers of a tetrafluoroethylene/2,2,4-trifluoro-5-trifluorometoxy-1,3-dioxole copolymer [Hyflon® AD60] were cut into 12.6 cm$^2$ stamps and tested in a permeation test-cell apparatus at 20–50° C. feed temperature, 165 psia feed pressure, and 15 psia permeate pressure with a 60% propylene/40% propane gas mixture. The saturation temperature of this mixture at 165 psia is 27° C. The gas fluxes were measured and the selectivities were calculated at each hour over the 5-hour test period at each temperature.

Fluxes and selectivities showed only minor changes over the test period. For example, at 30° C. feed temperature, the flux increased from 25 GPU to about 50 GPU over the 5-hour test period. The calculated selectivities decreased slightly from about 3.1 to about 2.7.

Example 5
Mixed-Gas Permeation Data

Composite membranes with a Hyflon® AD60 selective layer were rolled into a spiral-wound module, which was tested with a gas mixture comprising approximately 60% propylene and 40% propane at 30° C. at feed pressures ranging from 65 to 165 psia and 20 psia permeate pressure. The gas fluxes were measured and the selectivities were calculated at each pressure.

The propylene flux increased from about 6 GPU at 65 psia, to about 9 GPU at 115 psia, and to about 19 GPU at 165 psia. The propylene/propane selectivities remained essentially constant in the range 3.0 to 3.3 across the range of pressures.

As can be seen from the results of Examples 4–5, Hyflon® AD60 membranes are suitable for use in the process of the invention.

Example 6
Mixed-Gas Permeation Data

Composite membranes with selective layers of the polyimide (3,4,3',4'-biphenyltetracarboxylic dianhydride-2,4,6-m-phenylenediamine) [BPDA-TMPD] were cut into 12.6-cm$^2$ stamps and tested according to the same general procedures as in Example 1, with pure oxygen and nitrogen and a gas mixture of 50% propylene/50% propane. The feed temperature was 23° C., the feed pressure was 65 psia, and the permeate pressure was 15 psia. The gas fluxes of the membranes were measured, and the selectivities were calculated. Table 3 summarizes the fluxes and selectivities of the composite membranes.

TABLE 3

| Membrane | Pressure-Normalized Flux (GPU) | | | | Selectivity (–) | |
|---|---|---|---|---|---|---|
| Sample # | $O_2$ | $N_2$ | $C_3H_6$ | $C_3H_8$ | $O_2/N_2$ | $C_3H_6/C_3H_8$ |
| 1 | 27.4 | 7.2 | 45.8 | 24.1 | 3.8 | 1.9 |
| 2 | 18.2 | 3.8 | 14.7 | 5.3 | 4.8 | 2.8 |

Example 7
Mixed-Gas Permeation Data

Composite membranes with a selective layer of BPDA-TMPD were rolled into a spiral-wound module, which was tested with a 60% propylene/40% propane feed gas mixture at 16° C. and 60° C. feed temperatures, 75–95 psia feed pressure, and 15 psia permeate pressure. The pressure-normalized gas fluxes were measured. For both gases at the lower temperature, the fluxes increased sharply above 85 psia. Because the increases in the gas fluxes were proportionate, the calculated selectivities remained between about 2.5 to 4 across the pressure range.

As can be seen from the results of Examples 6–7, BPDA-TMPD membranes are suitable for use in the process of the invention.

Example 8
Mixed-Gas Permeation Data

Figure 3:
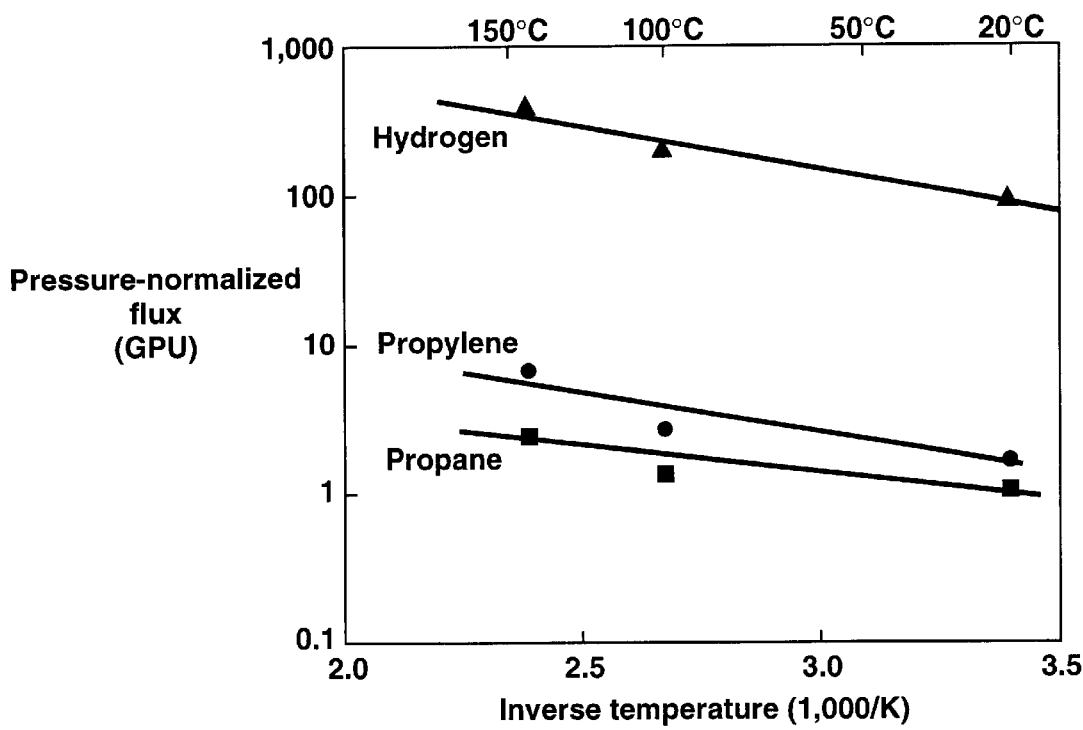
FIG. 3 is graph of mixed-gas pressure-normalized fluxes as a function of temperature with a Hyflon® AD60 membrane.
Figure 4:
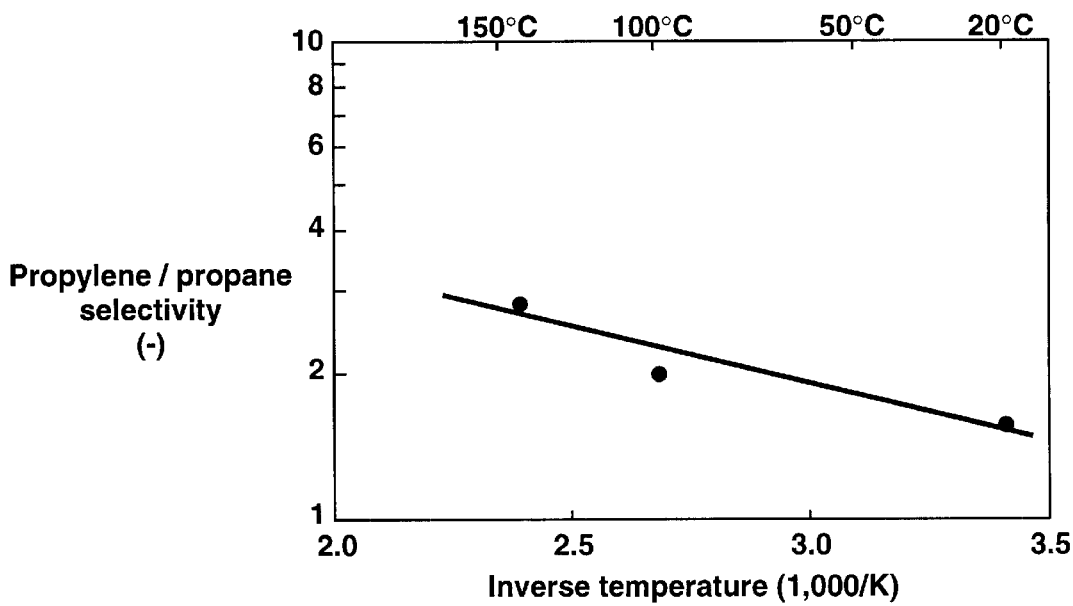
FIG. 4 is graph of mixed-gas selectivity as a function of temperature with a Hyflon® AD60 membrane.

A composite membrane with a selective layer of Hyflon® AD60 was cut into stamps and tested with a gas mixture of 80% hydrogen/15% propane/5% propylene. The feed pressure was 80 psia, the permeate pressure was 15 psia, and the feed temperature was varied from 20° C. to 170° C. The pressure-normalized gas fluxes were measured, and the selectivities calculated. The results are presented in FIGS. 3 and 4, graphs of the gas fluxes and the propylene/propane selectivity, respectively, as a function of feed temperature.

Example 9
Mixed-Gas Permeation Data

Figure 5:
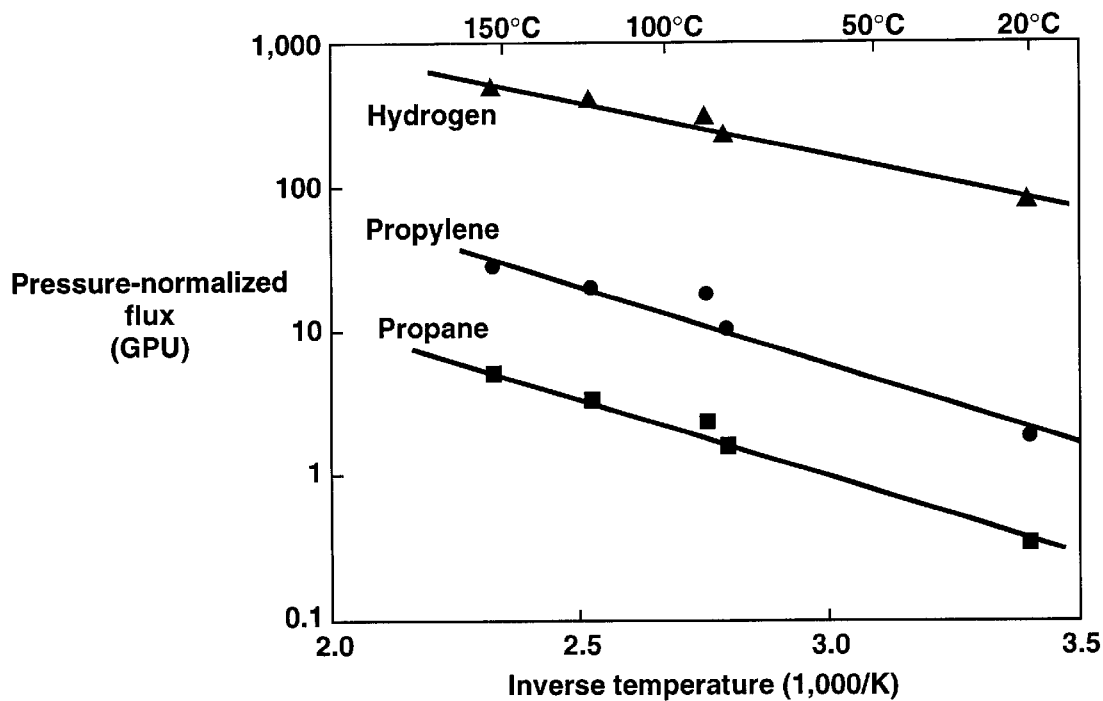
FIG. 5 is graph of mixed-gas pressure-normalized fluxes as a function of temperature with a BPDA-TMPD polyimide membrane.
Figure 6:
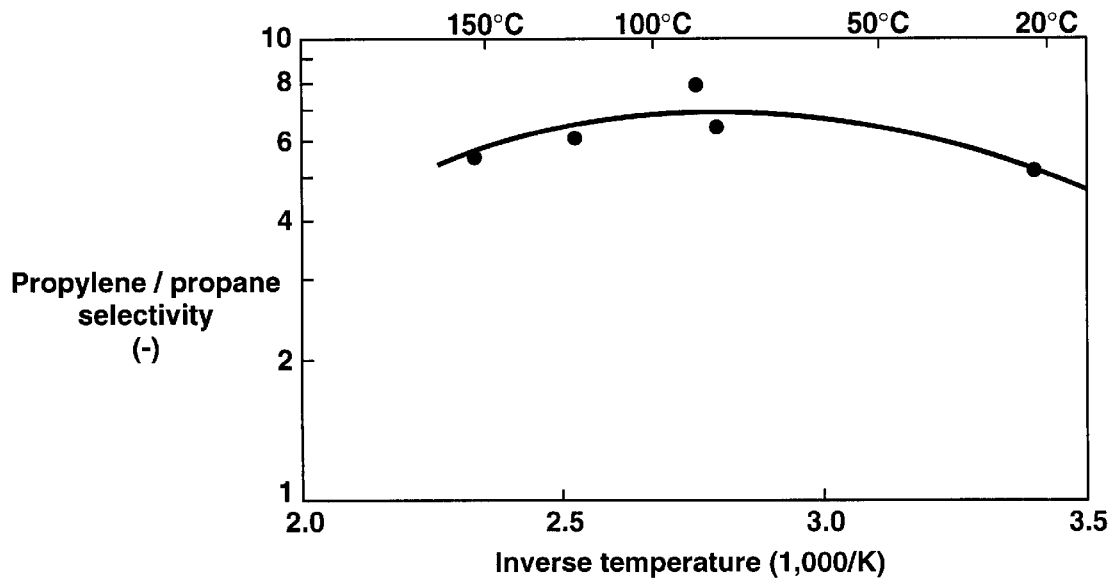
FIG. 6 is graph of mixed-gas selectivity as a function of temperature with a BPDA-TMPD polyimide membrane.

The experiment of Example 8 was repeated with a composite membrane with a selective layer of BPDA-TMPD. All experimental conditions were as in Example 8. The results are presented in FIGS. 5 and 6, graphs of the gas fluxes and the propylene/propane selectivity, respectively, as a function of feed temperature.

Example 10
Mixed-Gas Permeation Data

A polymer electrolyte membrane with a selective layer of poly(ethylene oxide)/silver tetrafluoroborate prepared as described in U.S. Pat. No. 5,670,051 was tested with a gas mixture of 50% propylene/50% propane. The feed temperature was 23° C., the feed pressures were 35, 50, and 65 psia, and the permeate pressure was 15 psia. The gas fluxes of the membranes were measured, and the selectivities calculated. Table 4 summarizes the fluxes and selectivities of the membrane.

TABLE 4

| Feed Pressure | Pressure-Normalized Flux (GPU) | | Selectivity (–) |
|---|---|---|---|
| (psia) | $C_3H_6$ | $C_3H_8$ | $C_3H_6/C_3H_8$ |
| 35 | 56 | 1.0 | 56 |
| 50 | 39 | 0.8 | 51 |
| 65 | 49 | 1.1 | 45 |

As can be seen, polymer electrolyte membranes of this type are suitable for use in the process of the invention.

Example 11
Olefin/Paraffin Separation

A computer calculation was performed with a modeling program, ChemCad V (ChemStations, Inc., Houston, Tex.), to illustrate just the performance of the membrane separation step 110 of FIG. 1, assuming for simplicity that membrane feedstream 109 contains 80% propylene and 20% propane only. The membrane unit, 110, was assumed to contain polymeric membranes as described in the detailed description of the invention. The membrane separation step produces propylene-depleted residue stream 111 for venting from the process, and propylene-enriched permeate stream 112 for recirculation to the reactor after recompression (not shown in FIG. 1). The membrane feed gas was assumed to be at 150 psia and 25° C. The results of the calculations are summarized in Table 5. Stream numbers refer to FIG. 1.

TABLE 5

| Stream | 109 | 111 | 112 |
|---|---|---|---|
| Mass Flow (lb/h) | 3,724 | 540 | 3,184 |
| Pressure (psia) | 150 | 150 | 15 |
| Temperature (° C.) | 25 | 24 | 25 |
| Component (lb/h) | | | |
| Propane | 773 | 307 | 467 |
| Propylene | 2,951 | 234 | 2,717 |
| Component (mol %): | | | |
| Propane | 20.0 | 55.6 | 14.1 |
| Propylene | 80.0 | 44.4 | 85.9 |

Membrane area = 2,598 m$^2$

As can be seen, the membrane separation step can reduce the propylene content of the vent gas stream from 80% to below 50%.

GROUP II EXAMPLES

Isopropyl Alcohol (Isopropanol)

Figure 7:
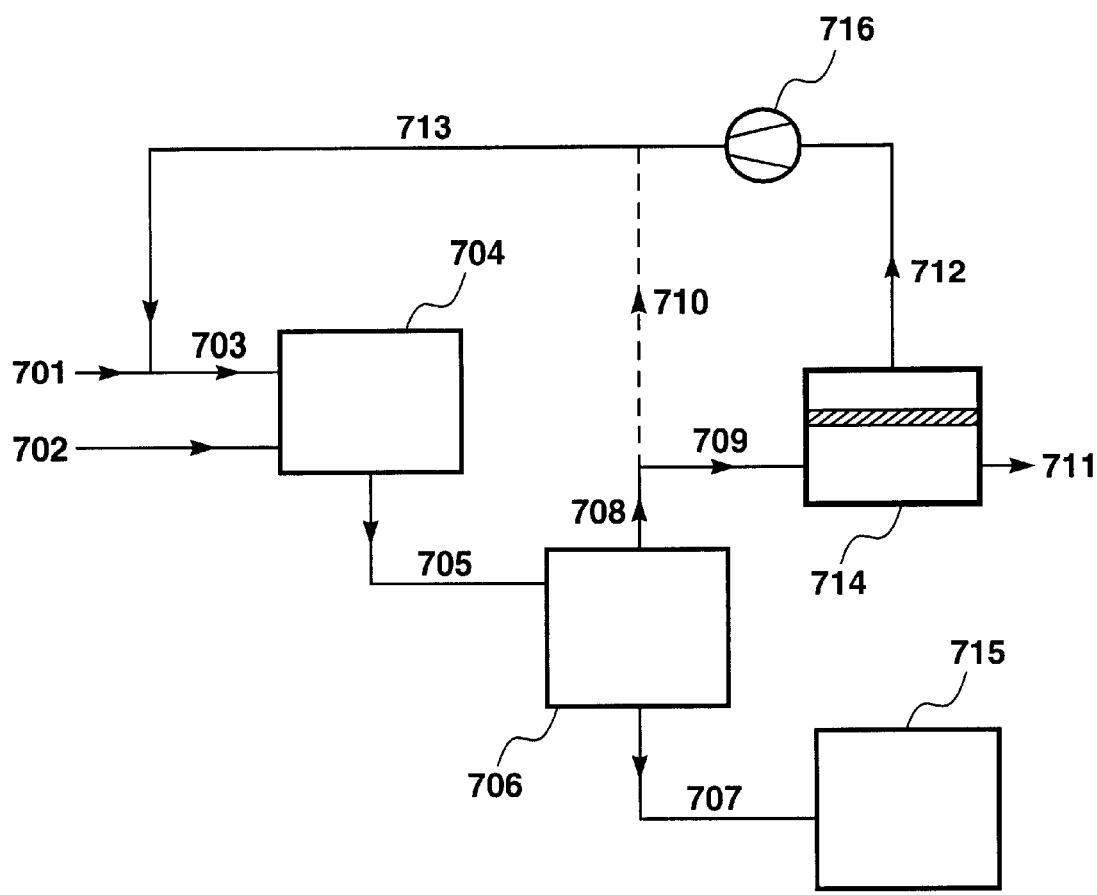
FIG. 7 is a schematic drawing of a isopropyl alcohol or cumene production process according to the invention.

In a typical isopropyl alcohol (IPA) manufacturing process using the direct hydration method, a process scheme as depicted in FIG. 7 is used. Propylene, stream 701, and water, stream 702, are passed into reactor 704 and reacted at 400–600 psia and 170–190° C. The rate of conversion is 40–60%, depending on the reactor conditions. The reactor effluent, stream 705, containing crude IPA, water, unreacted propylene, and inerts (mostly propane) is passed to the separator section, indicated as box 706. Here the effluent is cooled and the pressure lowered to 150–200 psia. The bottom fraction from this flash step is an aqueous solution, 707, containing IPA, which is sent for IPA recovery and purification by distillation, indicated as box 715.

The overhead stream from the flash column contains unreacted propylene, propane and the byproduct isopropyl ether. The isopropyl ether is fractionated from the light gases to produce overhead gas stream, 708, containing propylene and propane. Because the propylene conversion is relatively low in the reactor, the volume of the remaining propylene in the overhead stream is too large to be wasted as fuel. Part of stream 708, therefore, may be recompressed if necessary, and recirculated as stream 713 to the reactor inlet, where it is mixed with the incoming propylene feed gas to form reactor feed stream 703. To control the propane level in the reactor, a portion of the recycle stream is withdrawn from the reactor loop as stream 709.

Four sets of computer modeling calculations were run based on this exemplary process configuration. The process was assumed to use a fresh propylene feedstock of 95% propylene purity, the remainder propane. The fresh propylene feed flow rate was assumed to be 20,000 lb/h, and the propylene conversion rate per pass was assumed to be 50%. The first set of calculations was performed without the membrane separation step, 714, to represent a comparative prior art process. Sets 2–4 were run including the membrane separation step, and varying the proportion of overhead gas sent through the membrane separation step in each set, to represent the performance of the process of the invention under various conditions. In all calculations, the process parameters were set to vent the same amount of propane, about 1,045 lb/h, from the process.

Set 1. Examples 12–15
Not in Accordance with the Invention

A computer calculation was performed to model the process design of FIG. 7, omitting the membrane separation step. Thus, overhead gas stream 708 was assumed to be withdrawn as shown. To control propane build-up in the reactor, a part of that stream was assumed simply to be vented from the process as stream 709, and the remainder of the stream was assumed to be recirculated through stream 710 to streams 713 and 703. Calculations were repeated assuming that the split ratio of stream 708 between streams 709 and 710 is 10:90, 20:80, 30:70 and 100:0 (no recirculation, stream 710 absent). The results are summarized in Tables 6–9. Stream numbers refer to FIG. 7.

Example 12
(Vent Stream 10% of Overhead)

TABLE 6

| Stream | Feed Gas 701 | Reactor Feed 703 | Overhead Gas 708 | Vent Gas 709 |
|---|---|---|---|---|
| Composition (mol %) | | | | |
| Propylene | 95 | 77.7 | 63.5 | 63.5 |
| Propane | 5 | 22.3 | 36.5 | 36.5 |
| Composition (lb/hr) | | | | |
| Propylene | 18,955 | 34,463 | 17,231 | 1,723 |
| Propane | 1,045 | 10,376 | 10,367 | 1,037 |

Example 13
(Vent Stream 20% of Overhead)

TABLE 7

| Stream | Feed Gas 701 | Reactor Feed 703 | Overhead Gas 708 | Vent Gas 709 |
|---|---|---|---|---|
| Composition (mol%) | | | | |
| Propylene | 95 | 86.3 | 75.9 | 75.9 |
| Propane | 5 | 13.7 | 24.1 | 24.1 |
| Composition (lb/h) | | | | |
| Propylene | 18,955 | 31,591 | 15,796 | 3,159 |
| Propane | 1,045 | 5,242 | 5,245 | 1,049 |

Example 14
(Vent Stream 30% of Overhead)

TABLE 8

| Stream | Feed Gas 701 | Reactor Feed 703 | Overhead Gas 708 | Vent Gas 709 |
|---|---|---|---|---|
| Composition (mol%) | | | | |
| Propylene | 95 | 89.7 | 81.4 | 81.4 |
| Propane | 5 | 10.3 | 18.6 | 18.6 |
| Composition (lb/h) | | | | |
| Propylene | 18,955 | 29,161 | 14,580 | 4,374 |
| Propane | 1,045 | 3,490 | 3,492 | 1,048 |

Example 15

(Vent Stream 100% of Overhead)

TABLE 9

| Stream | Feed Gas 701 | Reactor Feed 703 | Overhead Gas 708 | Vent Gas 709 |
|---|---|---|---|---|
| Composition (mol%) | | | | |
| Propylene | 95 | 95 | 90.5 | 90.5 |
| Propane | 5 | 5 | 9.5 | 9.5 |
| Composition (lb/h) | | | | |
| Propylene | 18,955 | 18,955 | 9,477 | 9,477 |
| Propane | 1,045 | 1,045 | 1.045 | 1.045 |

As may be seen by comparing the tables, the greater the proportion of gas that is vented from the process, the higher can the concentration of propylene in the reactor feed be maintained. However, this is achieved at the expense of increasing propylene loss in the vent stream. In the extreme case that there is no recycle, the reactor feed propane content is held at 5%, but, at a propylene conversion per pass of only 50%, this results in loss of half of the feedstock, 9,477 lb/h of propylene, in the propane vent stream 709. In other words, for every 1 lb/h of propane that is vented, more than 9 lb/h of propylene is lost.

On the other hand, if only 10% of the overhead gas is vented and the remaining 90% is recirculated, the loss of propylene is cut to only 1.7 lb/h for 1 lb/h of propane vented. But in this case, the reactor feed concentration is driven down to only 78% propylene, which in a real process, would have a serious adverse effect on reactor productivity.

Set 2. Examples 16–22

Process of the Invention

A set of computer calculations was performed to model the process of the invention according to the design of FIG. 7, including the membrane system. As in Example 12, it was assumed that 10% of stream 708 is purged as stream 709 and 90% of stream 708 is recirculated directly to the reactor as stream 710. As shown in FIG. 7, stream 709 was assumed to be treated in membrane separation step 714, to yield a propylene-enriched permeate stream, 712, which is recompressed in compressor 716 and recirculated to the reactor feed, and a propane-enriched residue stream, 711, which is vented from the process.

The membrane area was varied from 100 m² to 1,000 m² to vary the performance of the membrane separation step. The results of the calculations are shown in Tables 10–15 and compiled in Table 16. Stream numbers refer to FIG. 7.

Example 16

TABLE 10

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 77.0 | 62.6 | 62.6 | 62.6 | 59.1 | 84.8 | 62.9 |
| Propane | 5.0 | 23.0 | 37.4 | 37.4 | 37.4 | 40.9 | 15.2 | 37.1 |
| Composition (lb/h) | | | | | | | | |
| Propylene | 18,955 | 35,051 | 17,526 | 1,753 | 15,773 | 1,429 | 323 | 16,096 |
| Propane | 1,045 | 10,974 | 10,964 | 1,096 | 9,868 | 1,036 | 60.6 | 9,928 |

Membrane area = 100 m²
Theoretical horsepower = 12 hp

Example 17

TABLE 11

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 76.2 | 61.5 | 61.5 | 61.5 | 54.1 | 83.2 | 62.1 |
| Propane | 5.0 | 23.8 | 38.5 | 38.5 | 38.5 | 45.9 | 16.8 | 37.9 |
| Composition (lb/h) | | | | | | | | |
| Propylene | 18,955 | 35,578 | 17,789 | 1,779 | 16,010 | 1,166 | 613 | 16,623 |
| Propane | 1,045 | 11,671 | 11,662 | 1,166 | 10,496 | 1,036 | 130 | 10,626 |

Membrane area = 200 m²
Theoretical horsepower = 23 hp

Example 18

TABLE 12

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 75.2 | 60.3 | 60.3 | 60.3 | 48.6 | 81.3 | 61.1 |
| Propane | 5.0 | 24.8 | 39.7 | 39.7 | 39.7 | 51.4 | 18.7 | 38.9 |
| Composition (lb/h) | | | | | | | | |
| Propylene | 18,955 | 36,037 | 18,019 | 1,802 | 16,217 | 936 | 866 | 17,083 |
| Propane | 1,045 | 12,458 | 12,449 | 1,245 | 11,204 | 1,036 | 209 | 11,413 |

Membrane area = 300 m$^2$
Theoretical horsepower = 33 hp

Example 19

TABLE 13

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 74.1 | 58.9 | 58.9 | 58.9 | 42.9 | 79.1 | 59.8 |
| Propane | 5.0 | 25.9 | 41.1 | 41.1 | 41.1 | 57.1 | 20.9 | 40.2 |
| Composition (lb/h) | | | | | | | | |
| Propylene | 18,955 | 36,425 | 18,213 | 1,821 | 16,392 | 742 | 1,079 | 17,471 |
| Propane | 1,045 | 13,349 | 13,339 | 1,334 | 12,005 | 1,035 | 299 | 12,303 |

Membrane area = 400 m$^2$
Theoretical horsepower = 43 hp

Example 20

TABLE 14

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 72.8 | 57.2 | 57.2 | 57.2 | 37.1 | 76.7 | 58.3 |
| Propane | 5.0 | 27.2 | 42.8 | 42.8 | 42.8 | 62.9 | 23.3 | 41.7 |
| Composition (lb/h) | | | | | | | | |
| Propylene | 18,955 | 36,739 | 18,370 | 1,837 | 16,533 | 585 | 1,252 | 17,785 |
| Propane | 1,045 | 14,382 | 14,376 | 1,438 | 12,938 | 1,039 | 399 | 13,337 |

Membrane area = 500 m$^2$
Theoretical horsepower = 51 hp

Example 21

TABLE 15

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 69.3 | 55.6 | 55.6 | 55.6 | 21.0 | 70.4 | 56.7 |
| Propane | 5.0 | 30.7 | 44.4 | 44.4 | 44.4 | 79.0 | 29.6 | 43.3 |
| Composition (lb/h) | | | | | | | | |
| Propylene | 18,955 | 42,037 | 23,347 | 2,335 | 21,012 | 265 | 2,070 | 23,083 |
| Propane | 1,045 | 19,524 | 19,520 | 1,952 | 17,568 | 1,041 | 911 | 18,479 |

Membrane area = 1,000 m$^2$
Theoretical horsepower = 91 hp

Example 22

The results of Examples 12 and 16–21 are compiled in Table 16, showing the improvement ylene recovery from the purge stream.

TABLE 16

| Exp. # | Membrane Area ($m^2$) | Compressor Theoretical HP | Propylene vented (lost) (lb/h) (Stream 711) | Propylene loss/lb propane vented (lb/h) | Propylene recovered (lb/h) (Stream 712) | Propane in reactor feed (%) (Stream 703) |
|---|---|---|---|---|---|---|
| 12 | — | — | 1,723 | 1.7 | — | 22.3 |
| 16 | 100 | 12 | 1,429 | 1.4 | 323 | 23.0 |
| 17 | 200 | 23 | 1,166 | 1.1 | 613 | 23.8 |
| 18 | 300 | 33 | 936 | 0.9 | 866 | 24.8 |
| 19 | 400 | 43 | 742 | 0.7 | 1,079 | 25.9 |
| 20 | 500 | 51 | 585 | 0.5 | 1,252 | 27.2 |
| 21 | 1,000 | 91 | 265 | 0.25 | 2,070 | 30.7 |

As can be seen from Table 16, the use of a membrane separation step can cut the propylene loss in relation to propane vented enormously. As in the prior art process exemplified in Examples 12–15, control of propylene loss is achieved at the expense of decreasing propylene content in the reactor feed gas. With the process of the invention, however, the trade-off is much less severe, in that the propylene loss can be cut by a factor of six or seven, with only an increase of 8% in the propane content of the feed mixture.

In the process of the invention, there is a further trade-off between the propylene recovery and the costs associated with the membrane separation step, in terms of membrane area used and compressor capacity required to recompress the permeate stream.

Set 3. Examples 23–29
Process of the Invention

A set of computer calculations was performed as in Examples 16–21, but this time assuming that 20% of stream 708 is purged as stream 709 for treatment in the membrane separation step and 80% of stream 708 is recirculated directly to the reactor as stream 710. The results of the calculations are shown in Tables 17–22 and compiled in Table 23.

Example 23

TABLE 17

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 86.1 | 75.6 | 75.6 | 75.6 | 73.8 | 91.5 | 76.0 |
| Propane | 5.0 | 13.9 | 24.4 | 24.4 | 24.4 | 26.2 | 8.5 | 24.0 |
| Composition (lb/h) | | | | | | | | |
| Propylene | 18,955 | 32,265 | 16,132 | 3,226 | 12,906 | 2,822 | 404 | 13,310 |
| Propane | 1,045 | 5,441 | 5,445 | 1,089 | 4,356 | 1,049 | 39.4 | 4,395 |

Membrane area = 100 $m^2$
Theoretical horsepower = 14 hp

Example 24

TABLE 18

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 85.9 | 75.3 | 75.3 | 75.3 | 71.4 | 90.9 | 76.0 |
| Propane | 5.0 | 14.1 | 24.7 | 24.7 | 24.7 | 28.6 | 9.1 | 24.0 |
| Composition (lb/h) | | | | | | | | |
| Propylene | 18,955 | 32,913 | 16,456 | 3,291 | 13,165 | 2,498 | 793 | 13,958 |
| Propane | 1,045 | 5,657 | 5,661 | 1,132 | 4,528 | 1,049 | 82.8 | 4,611 |

Membrane area = 200 $m^2$
Theoretical horsepower = 28 hp

Example 25

TABLE 19

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 85.7 | 75.0 | 75.0 | 75.0 | 68.8 | 90.4 | 76.0 |
| Propane | 5.0 | 14.3 | 25.0 | 25.0 | 25.0 | 31.2 | 9.6 | 24.0 |
| Composition (lb/h) | | | | | | | | |
| Propylene | 18,955 | 33,536 | 16,768 | 3,354 | 13,415 | 2,187 | 1,167 | 14,582 |
| Propane | 1,045 | 5,860 | 5,856 | 1,171 | 4,685 | 1,041 | 130 | 4,815 |

Membrane area = 300 m$^2$
Theoretical horsepower = 41 hp

Example 26

TABLE 20

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 85.3 | 74.3 | 74.3 | 74.3 | 65.4 | 89.6 | 75.6 |
| Propane | 5.0 | 14.7 | 25.7 | 25.7 | 25.7 | 34.6 | 10.4 | 24.4 |
| Composition (lb/h) | | | | | | | | |
| Propylene | 18,955 | 34,114 | 17,057 | 3,411 | 13,645 | 1,897 | 1,514 | 15,159 |
| Propane | 1,045 | 6,167 | 6,172 | 1,234 | 4,937 | 1,050 | 185 | 5,122 |

Membrane area = 400 m$^2$
Theoretical horsepower = 53 hp

Example 27

TABLE 21

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 84.9 | 73.7 | 73.7 | 73.7 | 61.9 | 88.7 | 75.2 |
| Propane | 5.0 | 15.1 | 26.3 | 26.3 | 26.3 | 38.1 | 11.3 | 24.8 |
| Composition (lb/h) | | | | | | | | |
| Propylene | 18,955 | 34,657 | 17,328 | 3,466 | 13,862 | 1,626 | 1,840 | 15,702 |
| Propane | 1,045 | 6,469 | 6,474 | 1,295 | 5,179 | 1,050 | 245 | 5,424 |

Membrane area = 500 m$^2$
Theoretical horsepower = 65 hp

Example 28

TABLE 22

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 81.8 | 69.2 | 69.2 | 69.2 | 39.1 | 82.7 | 71.2 |
| Propane | 5.0 | 18.2 | 30.8 | 30.8 | 30.8 | 60.9 | 17.3 | 28.8 |
| Composition (lb/h) | | | | | | | | |
| Propylene | 18,955 | 36,628 | 18,314 | 3,663 | 14,651 | 640 | 3,022 | 17,673 |
| Propane | 1,045 | 8,541 | 8,543 | 1,709 | 6,834 | 1,047 | 661 | 7,496 |

Membrane area = 1,000 m$^2$
Theoretical horsepower = 114 hp

Example 29

The results of Examples 13 and 23–28 are compiled in Table 23, showing the improvement in propylene recovery from the purge stream.

TABLE 23

| Exp. # | Membrane Area (m²) | Compressor Theoretical HP | Propylene vented (lost) (lb/h) (Stream 711) | Propylene loss/lb propane vented (lb/h) | Propylene recovered (lb/h) (Stream 712) | Propane in reactor feed (%) (Stream 703) |
|---|---|---|---|---|---|---|
| 13 | 0 | 0 | 3,159 | 3 | — | 13.7 |
| 23 | 100 | 14 | 2,822 | 2.7 | 404 | 13.9 |
| 24 | 200 | 28 | 2,498 | 2.4 | 793 | 14.1 |
| 25 | 300 | 41 | 2,187 | 2.1 | 1,167 | 14.3 |
| 26 | 400 | 53 | 1,897 | 1.8 | 1,514 | 14.7 |
| 27 | 500 | 65 | 1,626 | 1.5 | 1,840 | 15.1 |
| 28 | 1,000 | 114 | 640 | 0.6 | 3,022 | 18.2 |

Table 23 shows a similar pattern to Table 16 with respect to the improved trade-off between propylene loss and reactor feed composition of the process of the invention compared with the prior art.

Set 4. Examples 30–36
Process of the Invention

A set of computer calculations was performed as in Examples 16–21, but this time assuming that 30% of stream 708 is purged as stream 709 for treatment in the membrane separation step and 70% of stream 708 is recirculated directly to the reactor as stream 710. The results of the calculations are shown in Tables 24–29 and compiled in Table 30.

Example 30

TABLE 24

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 89.7 | 81.4 | 81.4 | 81.4 | 80.2 | 93.9 | 81.8 |
| Propane | 5.0 | 10.3 | 18.6 | 18.6 | 18.6 | 19.8 | 6.1 | 18.2 |
| Composition (lb/h) | | | | | | | | |
| Propylene | 18,955 | 29,838 | 14,919 | 4,476 | 10,443 | 4,035 | 440 | 10,884 |
| Propane | 1,045 | 3,579 | 3,577 | 1,073 | 2,504 | 1,043 | 30.0 | 2,534 |

Membrane area = 100 m²
Theoretical horsepower = 15 hp

Example 31

TABLE 25

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 89.7 | 81.3 | 81.3 | 81.3 | 78.8 | 93.6 | 82.1 |
| Propane | 5.0 | 10.3 | 18.7 | 18.7 | 18.7 | 21.2 | 6.4 | 17.9 |
| Composition (lb/h) | | | | | | | | |
| Propylene | 18,955 | 30,503 | 15,251 | 4,575 | 10,676 | 3,703 | 872 | 11,548 |
| Propane | 1,045 | 3,687 | 3,685 | 1,105 | 2,579 | 1,043 | 62.2 | 2,642 |

Membrane area = 200 m²
Theoretical horsepower = 29 hp

Example 32

TABLE 26

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 89.6 | 81.1 | 81.1 | 81.1 | 77.2 | 93.3 | 82.3 |
| Propane | 5.0 | 10.4 | 18.9 | 18.9 | 18.9 | 22.8 | 6.7 | 17.7 |
| Composition (lb/h) | | | | | | | | |
| Propylene | 18,955 | 31,152 | 15,576 | 4,673 | 10,903 | 3,379 | 1,294 | 12,197 |
| Propane | 1,045 | 3,802 | 3,800 | 1,140 | 2,660 | 1,043 | 96.9 | 2,757 |

Membrane area = 300 m$^2$
Theoretical horsepower = 44 hp

Example 33

TABLE 27

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 89.5 | 80.9 | 80.9 | 80.9 | 75.5 | 93.0 | 82.3 |
| Propane | 5.0 | 10.5 | 19.1 | 19.1 | 19.1 | 24.5 | 7.0 | 17.7 |
| Composition (lb/h) | | | | | | | | |
| Propylene | 18,955 | 31,785 | 15,893 | 4,768 | 11,125 | 3,063 | 1,705 | 12,830 |
| Propane | 1,045 | 3,927 | 3,924 | 1,177 | 2,747 | 1,043 | 135 | 2,882 |

Membrane area = 400 m$^2$
Theoretical horsepower = 58 hp

Example 34

TABLE 28

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 89.3 | 80.7 | 80.7 | 80.7 | 73.5 | 92.6 | 82.3 |
| Propane | 5.0 | 10.7 | 19.3 | 19.3 | 19.3 | 26.5 | 7.4 | 17.7 |
| Composition (lb/h) | | | | | | | | |
| Propylene | 18,955 | 32,397 | 16,199 | 4,860 | 11,339 | 2,756 | 2,103 | 13,442 |
| Propane | 1,045 | 4,065 | 4,063 | 1,219 | 2,844 | 1,043 | 176 | 3,019 |

Membrane area = 500 m$^2$
Theoretical horsepower = 72 hp

Example 35

TABLE 29

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 88.0 | 78.6 | 78.6 | 78.6 | 58.9 | 89.9 | 81.0 |
| Propane | 5.0 | 12.0 | 21.4 | 21.4 | 21.4 | 41.1 | 10.1 | 19.0 |
| Composition (lb/h) | | | | | | | | |
| Propylene | 18,955 | 35,039 | 17,519 | 5,256 | 12,263 | 1,434 | 3,821 | 16,084 |
| Propane | 1,045 | 4,999 | 5,002 | 1,501 | 3,501 | 1,049 | 452 | 3,953 |

Membrane area = 1,000 m$^2$
Theoretical horsepower = 133 hp

Example 36

The results of Examples 14 and 30–35 are compiled in Table 30, showing the improvement propylene recovery from the purge stream.

TABLE 30

| Exp. # | Membrane Area (m²) | Compressor Theoretical HP | Propylene vented (lost) (lb/h) (Stream 711) | Propylene loss/lb propane vented (lb/h) | Propylene recovered (lb/h) (Stream 712) | Propane in reactor feed (%) (Stream 703) |
|---|---|---|---|---|---|---|
| 14 | 0 | 0 | 4,374 | 4.2 | — | 10.3 |
| 30 | 100 | 15 | 4,035 | 3.9 | 440 | 10.3 |
| 31 | 200 | 29 | 3,703 | 3.5 | 872 | 10.3 |
| 32 | 300 | 44 | 3,379 | 3.2 | 1,294 | 10.4 |
| 33 | 400 | 58 | 3,063 | 2.9 | 1,705 | 10.5 |
| 34 | 500 | 72 | 2,756 | 2.6 | 2,103 | 10.7 |
| 35 | 1,000 | 133 | 1,434 | 1.4 | 3,821 | 12.0 |

Example 37

Figure 8:
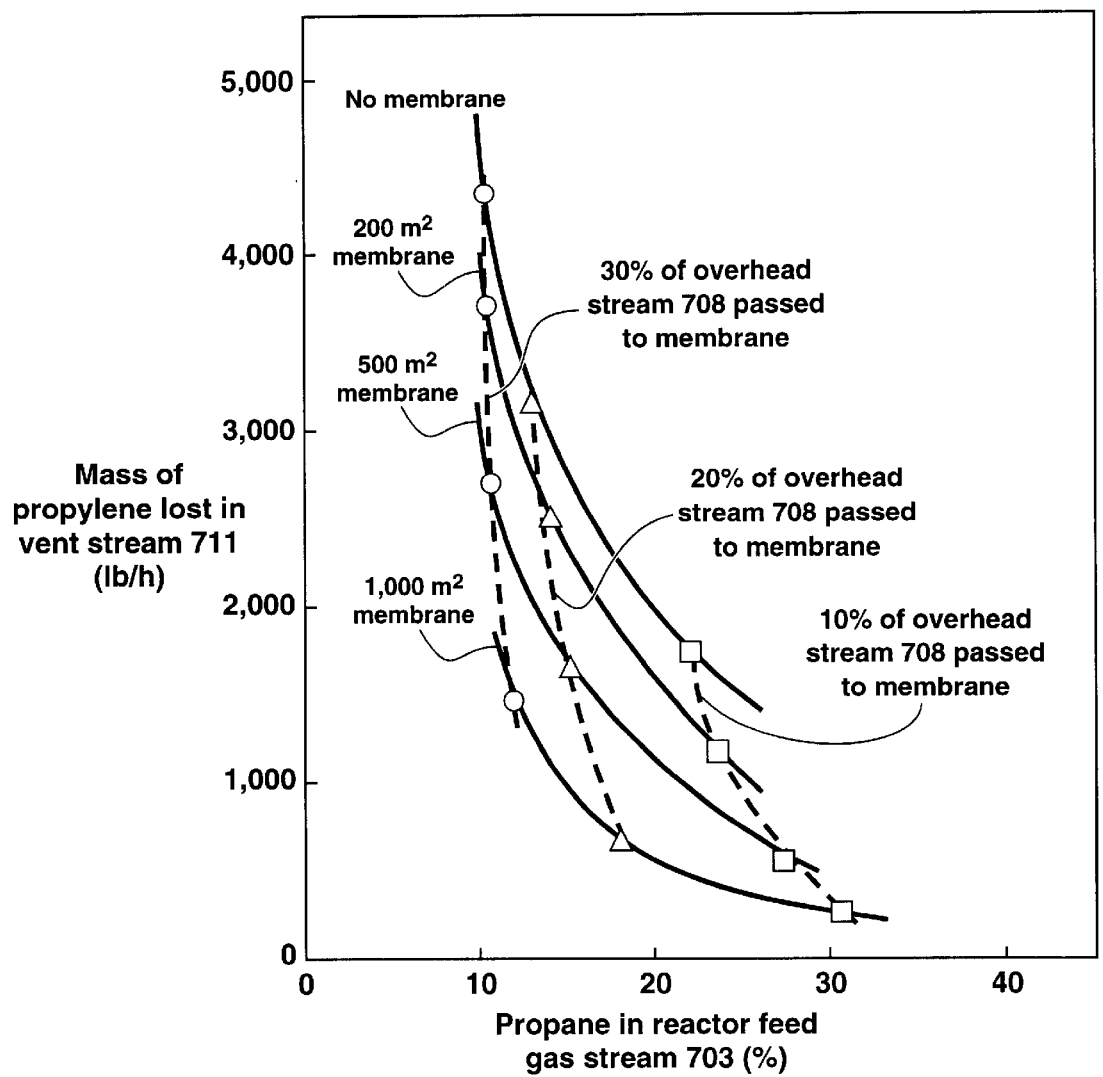
FIG. 8 is a graph showing the amount of propylene vented as a function of percent propane in the reactor feed in an isopropyl alcohol production process according to the invention.

The calculated results for propylene loss in the vent stream and propane content of the reactor feed stream compiled in Tables 16, 23, and 30 were used to plot the curves shown in FIG. 8. The data in those tables corresponding to the "no membrane" and membrane area 200 m², 500 m², and 1,000 m² cases were plotted.

When the gas withdrawn from the overhead recycle loop is simply vented without membrane treatment, the trade-off, effected by varying the relative proportions of gas that are recycled and vented, between propylene loss and reactor propane content is represented by the uppermost curve.

The improvement brought about by the process of the invention can now be seen very clearly. In an idealized process where the feed was 100% pure propylene, the process could be run without propylene loss by simply recirculating all of the unreacted propylene until it had all been converted. This hypothetical ideal would be represented by a point at the origin of the graph. When a membrane separation step is integrated into the IPA manufacturing process, the trade-off curve is shifted toward this point of zero propane content in the reactor combined with zero propylene loss. The larger the membrane area that is used, the closer does the process approach the ideal.

GROUP III EXAMPLES

Cumene

In a typical cumene manufacturing process using a vapor-phase reaction, a process scheme as depicted in FIG. 7 is used. Propylene, stream 701, and benzene, stream 702, are passed into reactor 704 and reacted at 200–500 psia and 200–250° C. The rate of propylene conversion is high, 90% or better, depending on the reactor conditions. The reactor effluent, stream 705, containing crude cumene, unreacted benzene and propylene, and inerts (mostly propane) is sent to the separation step or series of steps, indicated as box 706. Here, the effluent stream is passed through a depropanizer column, to yield light overhead gas stream 708, and then through a benzene recovery column, where benzene is separated for recirculation to the reactor. The bottom stream from the benzene recovery column forms crude product stream 707, which is sent for cumene separation from heavier byproducts by distillation, indicated as box 715.

Part of stream 708 may be recompressed if necessary and is recirculated as stream 710 and 713 to the reactor inlet, where it is mixed with the incoming propylene feed gas to form reactor feed stream 703. To control the propane level in the reactor, a portion of the recycle stream is withdrawn from the reactor loop as stream 709.

Three sets of computer modeling calculations were run based on this exemplary process configuration. The process was assumed to use a fresh propylene feedstock of 95% propylene purity, the remainder propane. The fresh propylene feed flow rate was assumed to be 10,000 lb/h, and the propylene conversion rate per pass was assumed to be 95%. The first set of calculations was performed without the membrane separation step, 714, to represent a comparative prior art process. Sets 2–3 were run including the membrane separation step, and varying the proportion of overhead gas sent through the membrane separation step in each set, to represent the performance of the process of the invention under various conditions. Set 2 assumed a propylene/propane selectivity in the membrane separation step of 3; Set 3 assumed a propylene/propane selectivity in the membrane separation step of 5. In all calculations, the process parameters were set to vent the same amount of propane, about 523 lb/h, from the process.

Set 1. Examples 38–42
Not in Accordance with the Invention

A computer calculation was performed to model the process design of FIG. 7, omitting the membrane separation step. Thus, overhead gas stream 708 was assumed to be withdrawn as shown. To control propane build-up in the reactor, a part of that stream was assumed simply to be vented from the process as stream 709, and the remainder of the stream was assumed to be recirculated through stream 710 to streams 713 and 703. Calculations were repeated assuming that the split ratio of stream 708 between streams 709 and 710 is 100:0 (no recirculation, stream 710 absent), 80:20, 60:40 and 40:60. The results are shown in Tables 31–34, and compiled in Table 35. Stream numbers refer to FIG. 7.

Example 38
(Vent Stream 100% of Overhead)

TABLE 31

| Stream | Feed Gas 701 | Reactor Feed 703 | Overhead Gas 708 | Vent Gas 709 |
|---|---|---|---|---|
| Composition (mol%) | | | | |
| Propylene | 95 | 95 | 48.7 | 48.7 |
| Propane | 5 | 5 | 51.3 | 51.3 |

TABLE 31-continued

| Stream | Feed Gas 701 | Reactor Feed 703 | Overhead Gas 708 | Vent Gas 709 |
|---|---|---|---|---|
| Composition (lb/h) | | | | |
| Propylene | 9,477 | 9,477 | 474 | 474 |
| Propane | 523 | 523 | 523 | 523 |

Example 39

(Vent Stream 80% of Overhead)

TABLE 32

| Stream | Feed Gas 701 | Reactor Feed 703 | Overhead Gas 708 | Vent Gas 709 |
|---|---|---|---|---|
| Composition (mol%) | | | | |
| Propylene | 95 | 93.9 | 43.4 | 43.4 |
| Propane | 5 | 6.1 | 56.6 | 56.6 |
| Composition (lb/h) | | | | |
| Propylene | 9,477 | 9,573 | 479 | 383 |
| Propane | 523 | 653 | 653 | 523 |

Example 40

(Vent Stream 60% of Overhead)

TABLE 33

| Stream | Feed Gas 701 | Reactor Feed 703 | Overhead Gas 708 | Vent Gas 709 |
|---|---|---|---|---|
| Composition (mol %) | | | | |
| Propylene | 95 | 92.1 | 36.8 | 36.8 |
| Propane | 5 | 7.9 | 63.2 | 63.2 |
| Composition (lb/h) | | | | |
| Propylene | 9,477 | 9,671 | 483 | 290 |
| Propane | 523 | 871 | 871 | 522 |

Example 41

(Vent Stream 40% Overhead)

TABLE 34

| Stream | Feed Gas 701 | Reactor Feed 703 | Overhead Gas 708 | Vent Gas 709 |
|---|---|---|---|---|
| Composition (mol %) | | | | |
| Propylene | 95 | 88.7 | 28.2 | 28.2 |
| Propane | 5 | 11.3 | 71.8 | 71.8 |
| Composition (lb/h) | | | | |
| Propylene | 9,477 | 9,770 | 489 | 195 |
| Propane | 523 | 1,306 | 1,305 | 522 |

Example 42

The results of Examples 38–41 are compiled in Table 35, showing the improvement in propylene recovery from the purge stream.

TABLE 35

| Exp. # | Split ratio (recycle/ purge) (%) | Propylene vented (lost) (lb/h) (Stream 709) | Propylene concentration (%) (Stream 709) | Propylene recovered (lb/h) (Stream 710/713) | Propane in reactor feed (%) (Stream 703) |
|---|---|---|---|---|---|
| 30 | 0/100 | 474 | 48.7 | — | 5.0 |
| 39 | 20/80 | 383 | 43.4 | 95.7 | 6.1 |
| 40 | 40/60 | 290 | 36.8 | 193 | 7.9 |
| 41 | 60/40 | 195 | 28.2 | 293 | 11.3 |

As may be seen, just as in the IPA calculations, the lower the propylene loss, the higher is the propane concentration in the reactor feed stream. Control over the propane concentration in the reactor is achieved at the expense of increasing propylene loss in the vent stream.

Set 2. Examples 43–46

Process of the Invention (Membrane Propylene/propane Selectivity 3)

A set of computer calculations was performed to model the process of the invention according to the design of FIG. 7, including the membrane system. The process parameters were set to match the vent stream of Example 41, that is, propylene loss of about 195 lb/h and propane loss of about 523 lb/h. As shown in FIG. 7, stream 709 was assumed to be treated in membrane separation step 714, to yield propylene-enriched permeate stream, 712, which is recompressed in compressor 716 and recirculated to the reactor feed, and propane-enriched residue stream, 711, which is vented from the process.

The split of stream 708 between streams 709 and 710 was varied from 100:0 (no direct recycle) to 60:40 (40% direct recycle). The results of the calculations are shown in Tables 36–38 and compiled in Table 39. Stream numbers refer to FIG. 7.

Example 43

(Stream 709 100% of Overhead)

TABLE 36

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 93.3 | 41.0 | 41.0 | — | 28.2 | 59.0 | 59.0 |
| Propane | 5.0 | 6.7 | 59.0 | 59.0 | — | 71.8 | 41.0 | 41.0 |
| Composition (lb/h) | | | | | | | | |
| Propylene | 9,477 | 9,770 | 488 | 488 | — | 196 | 292 | 292 |
| Propane | 523 | 735 | 735 | 735 | — | 523 | 212 | 212 |

Membrane Area = 216 m$^2$
Theoretical Compressor hp = 15 hp

Example 44

(Stream 709 80% of Overhead)

TABLE 37

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 92.4 | 37.7 | 37.7 | 37.7 | 28.2 | 56.9 | 48.6 |
| Propane | 5.0 | 7.6 | 62.3 | 62.3 | 62.3 | 71.8 | 43.1 | 51.4 |
| Composition (lb/h) | | | | | | | | |
| Propylene | 9,477 | 9,770 | 488 | 391 | 97.7 | 196 | 195 | 293 |
| Propane | 523 | 846 | 846 | 677 | 169 | 523 | 154 | 324 |

Membrane Area = 153 m$^2$
Theoretical Compressor hp = 11 hp

Example 45

(Stream 709 60% of Overhead)

TABLE 38

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 91.0 | 33.5 | 33.5 | 33.5 | 28.2 | 54.3 | 38.4 |
| Propane | 5.0 | 9.0 | 66.5 | 66.5 | 66.5 | 71.8 | 45.7 | 61.6 |
| Composition (lb/h) | | | | | | | | |
| Propylene | 9,477 | 9,770 | 489 | 293 | 195 | 196 | 97.4 | 293 |
| Propane | 523 | 1,014 | 1,014 | 609 | 406 | 523 | 85.9 | 492 |

Membrane Area = 83 m$^2$
Theoretical Compressor hp = 6 hp

Example 46

The results of Examples 41 and 43–45 are compiled in Table 39.

TABLE 39

| Exp. # | Split ratio (recycle/purge) (%) | Membrane Area (m$^2$) | Theoretical Compressor HP | Propylene recovered (lb/h) (Stream 712) | Propane in reactor feed (%) (Stream 703) |
|---|---|---|---|---|---|
| 41 | 60/40 | — | — | — | 11.3 |
| 45 | 40/60 | 83 | 6 | 97.4 | 9.0 |
| 44 | 20/80 | 153 | 11 | 195 | 7.6 |
| 43 | 0/100 | 216 | 15 | 292 | 6.7 |

As can be seen clearly from Table 39, the presence of the membrane separation step alters the trade-off between propylene loss and reactor feed composition substantially. In each case, the propylene loss is contained at a level the same as that achieved in the "no membrane" case that relied on 60% direct recycle. However, while the propylene loss is thus contained, the concentration of propane in the reactor feed stream is driven down from 11.3% in the "no membrane" case, to only 6.7% in the case in which all of the purge gas is subjected to the membrane separation treatment.

Set 3. Examples 47–50
Process of the Invention (Membrane Propylene/propane Selectivity 5)

The calculations of set 2 were repeated, this time assuming that the membranes used in the membrane separation step had a propylene/propane selectivity of 5. The process parameters were again chosen to achieve a propylene loss of about 195 lb/h and a propane loss of about 523 lb/h, and the calculations were repeated for various splits of stream 708 into streams 709 and 710. The results of the calculations are shown in Tables 40–42 and compiled in Table 43. Stream numbers refer to FIG. 7.

Example 47

(Stream 709 100% of Overhead)

TABLE 40

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 94.0 | 44.1 | 44.1 | — | 28.2 | 71.0 | 71.0 |
| Propane | 5.0 | 6.0 | 55.9 | 55.9 | — | 71.8 | 29.0 | 29.0 |
| Composition (lb/h) | | | | | | | | |
| Propylene | 9,477 | 9,770 | 488 | 488 | — | 196 | 292 | 292 |
| Propane | 523 | 648 | 648 | 648 | — | 523 | 125 | 125 |

Membrane Area = 128 m$^2$
Theoretical Compressor hp = 13 hp

Example 48

(Stream 709 80% of Overhead)

TABLE 41

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 93.0 | 40.0 | 40.0 | 40.0 | 28.2 | 68.7 | 55.4 |
| Propane | 5.0 | 7.0 | 60.0 | 60.0 | 60.0 | 71.8 | 31.3 | 44.6 |

TABLE 41-continued

| Stream | 701 | 703 | 708 | 709 | 710 | 711 | 712 | 713 |
|---|---|---|---|---|---|---|---|---|
| Composition (lb/h) | | | | | | | | |
| Propylene | 9,477 | 9,770 | 489 | 391 | 97.7 | 196 | 195 | 293 |
| Propane | 523 | 770 | 770 | 616 | 154 | 523 | 93.3 | 247 |

Membrane Area = 92 m$^2$
Theoretical Compressor hp = 9 hp

Example 49
(Stream 709 60% of Overhead)

TABLE 42

| Stream | 701 | 703 | 708 | 709 | 710 | 711 | 712 | 713 |
|---|---|---|---|---|---|---|---|---|
| Composition (mol %) | | | | | | | | |
| Propylene | 95.0 | 91.4 | 34.8 | 34.8 | 34.8 | 28.2 | 65.8 | 41.2 |
| Propane | 5.0 | 8.6 | 65.2 | 65.2 | 65.2 | 71.8 | 34.2 | 58.8 |
| Composition (lb/h) | | | | | | | | |
| Propylene | 9,477 | 9,770 | 488 | 293 | 195 | 196 | 97.3 | 293 |
| Propane | 523 | 960 | 960 | 576 | 384 | 523 | 53.1 | 437 |

Membrane Area = 51 m$^2$
Theoretical Compressor hp = 5 hp

Example 50

The results of Examples 41 and 47–49 are compiled in Table 43.

TABLE 43

| Exp. # | Split ratio (recycle/ purge) (%) | Membrane Area (m$^2$) | Theoretical Compressor HP | Propylene recovered (lb/h) (Stream 712) | Propane in reactor feed (%) (Stream 703) |
|---|---|---|---|---|---|
| 41 | 60/40 | — | — | — | 11.3 |
| 49 | 40/60 | 51 | 5 | 97.3 | 8.6 |
| 48 | 20/80 | 92 | 9 | 195 | 7.0 |
| 47 | 0/100 | 128 | 13 | 292 | 6.0 |

Table 43 shows the same trend as Table 39, that is, the membrane separation treatment enables the propane content of the reactor feed stream to be driven down without increasing propylene loss. In this case, when all of the overhead gas is purged through the membrane separation unit, the propylene loss of 195 lb/h, as low as the best "no membrane" case, is accompanied by a propane concentration in the reactor feed of only 6%, almost half the comparable concentration achieved in the prior art process.

Comparing Tables 39 and 43, it can be seen that even a membrane step with very modest performance provides a very beneficial improvement to the cumene manufacturing process. If the membrane step is more selective, the benefits are greater.

GROUP IV

Propylene Oxide

Figure 9:
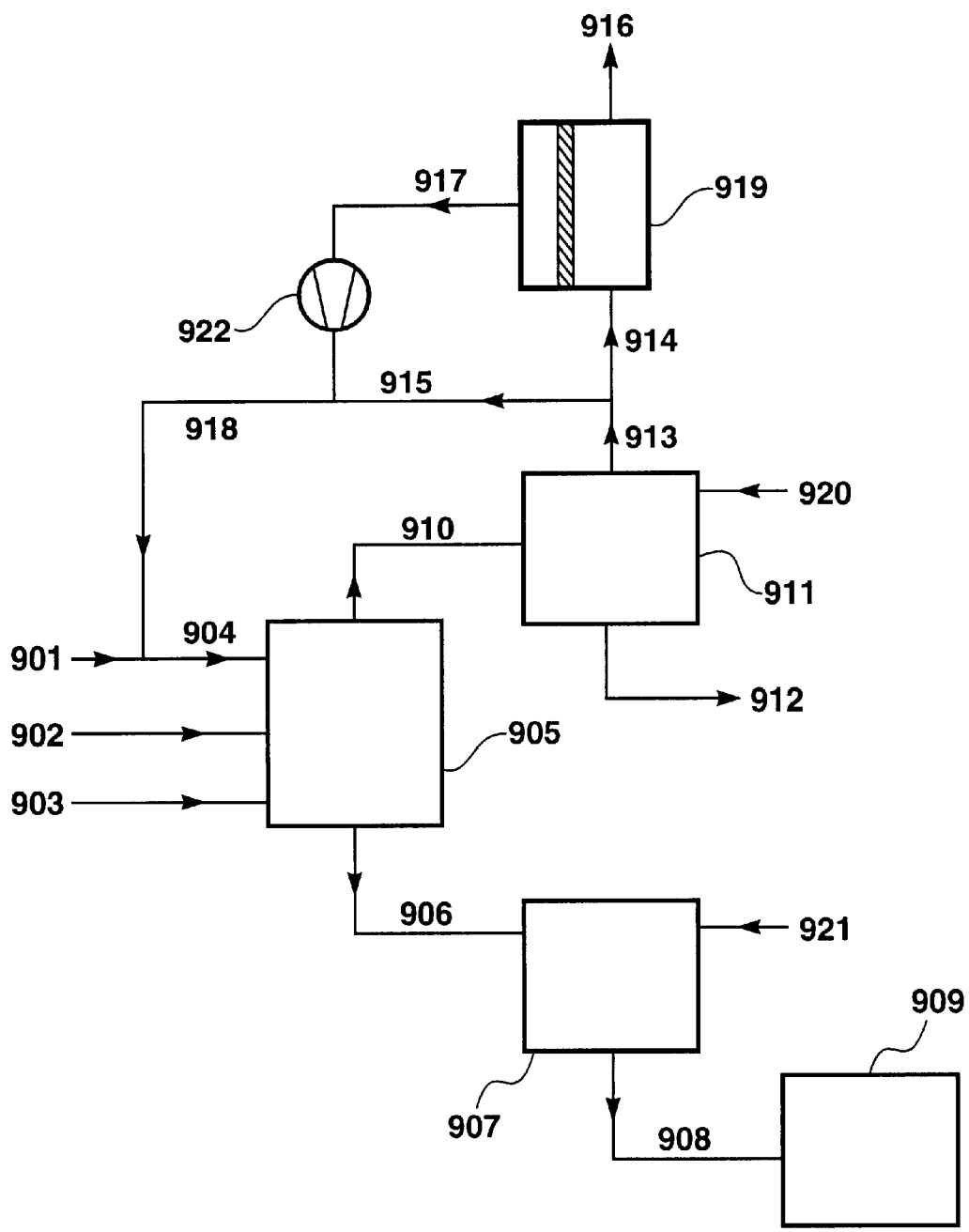
FIG. 9 is a schematic drawing of a propylene oxide production process according to the invention.

In a typical propylene oxide manufacturing process by chlorohydrination, a process scheme as depicted in FIG. 9 is used. Propylene, stream 901, water, stream 902, and chlorine, stream 903, are passed into reactor 905. The chlorohydrin solution produced in the reactor is withdrawn as stream 906, and passed to reactor 907, where the chlorohydrin reacts with calcium hydroxide, introduced in stream 921, to produce crude propylene oxide stream 908. This stream is sent to separation and purification by distillation, indicated overall as box 909. The light overhead stream, 910, from the reactor is sent to scrubber 911, where it is scrubbed with sodium hydroxide, introduced as stream 920. An aqueous waste stream is removed as stream 912.

The remaining light overhead gas, stream 913, containing unreacted propylene and propane, is withdrawn from the top of the scrubber. Part of stream 913 is recirculated as streams 915 and 918 to the reactor inlet, where it is mixed with the incoming propylene feed gas to form reactor feed stream 904. To control the propane level in the reactor, a portion of the recycle stream is withdrawn from the reactor loop as stream 914.

Three sets of computer modeling calculations were run based on this exemplary process configuration. The process was assumed to use a fresh propylene feedstock of 95% propylene purity, the remainder propane. The fresh propylene feed flow rate was assumed to be 20,000 lb/h, and the propylene conversion rate per pass was assumed to be 65%. In all calculations, the process parameters were set to vent the same amount of propane, about 1,045 lb/h, from the process.

The first set of calculations was performed without the membrane separation step, 919, to represent a comparative prior art process.

Sets 2 and 3 were run including the membrane separation step, and varying the proportion of gas sent through the membrane separation step in each set, to represent the performance of the process of the invention under various conditions.

For Set 2, the split between streams 915 and 914 was varied from 90:10 to 60:40, and for each split, calculations were run for different membrane areas.

For Set 3, the propylene and propane losses in the vent stream were fixed, and the split and membrane area were varied to show the effect on propane content of the reactor feed stream.

Set 1. Examples 51–55

Not in Accordance with the Invention

A computer calculation was performed to model the process design of FIG. 9, omitting the membrane separation step. Thus, overhead gas stream 913 was assumed to be withdrawn as shown. To control propane build-up in the reactor, a part of stream 913 was assumed simply to be vented from the process as stream 914, and the remainder of the stream was assumed to be recirculated through stream 915 to streams 918 and 904. Calculations were repeated assuming that the split ratio of stream 913 between streams 914 and 915 is 10:90 (10% of stream 913 vented), 20:80 (20% of stream 913 vented), 30:70 (30% of stream 913 vented), and 40:60 (40% of stream 913 vented). The results are shown in Tables 44–47 and compiled in Table 48. Stream numbers refer to FIG. 9.

Example 51

(Vent Stream 10% of Overhead)

TABLE 44

| Stream | Feed Gas 901 | Reactor Feed 904 | Overhead Gas 913 | Vent Gas 914 | Recycle Gas 915 |
|---|---|---|---|---|---|
| Composition (mol %) | | | | | |
| Propylene | 95 | 73.4 | 49.0 | 49.0 | 49.0 |
| Propane | 5 | 26.6 | 51.0 | 51.0 | 51.0 |
| Composition (lb/h) | | | | | |
| Propylene | 18,955 | 27,671 | 9,685 | 968 | 8,716 |
| Propane | 1,045 | 10,534 | 10,543 | 1,054 | 9,489 |

Example 52

(Vent Stream 20% of Overhead)

TABLE 45

| Stream | Feed Gas 901 | Reactor Feed 904 | Overhead Gas 913 | Vent Gas 914 | Recycle Gas 915 |
|---|---|---|---|---|---|
| Composition (mol %) | | | | | |
| Propylene | 95 | 84.1 | 65.0 | 65.0 | 65.0 |
| Propane | 5 | 15.9 | 35.0 | 35.0 | 35.0 |
| Composition (lb/h) | | | | | |
| Propylene | 18,955 | 26,326 | 9,214 | 1,843 | 7,371 |
| Propane | 1,045 | 5,213 | 5,209 | 1,042 | 4,167 |

Example 53

(Vent Stream 30% of Overhead)

TABLE 46

| Stream | Feed Gas 901 | Reactor Feed 904 | Overhead Gas 913 | Vent Gas 914 | Recycle Gas 915 |
|---|---|---|---|---|---|
| Composition (mol %) | | | | | |
| Propylene | 95 | 88.3 | 72.5 | 72.5 | 72.5 |
| Propane | 5 | 11.7 | 27.5 | 27.5 | 27.5 |
| Composition (lb/h) | | | | | |
| Propylene | 18,955 | 25,105 | 8,787 | 2,636 | 6,151 |
| Propane | 1,045 | 3,489 | 3,491 | 1,047 | 2,443 |

Example 54

(Vent Stream 40% of Overhead)

TABLE 47

| Stream | Feed Gas 901 | Reactor Feed 904 | Overhead Gas 913 | Vent Gas 914 | Recycle Gas 915 |
|---|---|---|---|---|---|
| Composition (mol %) | | | | | |
| Propylene | 95 | 90.6 | 77.1 | 77.1 | 77.1 |
| Propane | 5 | 9.4 | 22.9 | 22.9 | 22.9 |
| Composition (lb/h) | | | | | |
| Propylene | 18,955 | 23,993 | 8,398 | 3,359 | 5,039 |
| Propane | 1,045 | 2,616 | 2,617 | 1,047 | 1,570 |

Example 55

The results of Examples 51–54 are compiled in Table 48.

TABLE 48

| Exp. # | Recycle/ Purge Split (%) | Propylene vented (lost) (lb/h) (Stream 914) | Propylene concentration (%) (Stream 914) | Propane in reactor feed (%) (Stream 914) |
|---|---|---|---|---|
| 51 | 90/10 | 968 | 49.0 | 26.6 |
| 52 | 80/20 | 1,843 | 65.0 | 15.9 |
| 53 | 70/30 | 2,636 | 72.5 | 11.7 |
| 54 | 60/40 | 3,359 | 77.1 | 9.4 |

The tables show the now familiar trade-off between propylene loss in the vent gas and propane concentration in the reactor feed.

Set 2. Examples 56–59

Process of the Invention; 10% of Overhead Treated by Membrane

A set of computer calculations was performed to model the process of the invention according to the design of FIG. 9, including the membrane system. As in Example 51, it was assumed that 10% of stream 913 is purged as stream 914 and 90% of stream 913 is recirculated directly to the reactor as stream 915. As shown in FIG. 9, stream 914 was assumed to be treated in membrane separation step 919, to yield propylene-enriched permeate stream, 917, for recirculation to the reactor feed after recompression in compressor 922, and propane-enriched residue stream, 916, for venting from the process.

The membrane area was varied from 200 m² to 1,000 m² to vary the performance of the membrane separation step. The results of the calculations are shown in Tables 49–51 and compiled in Table 52. Stream numbers refer to FIG. 9.

Example 56

TABLE 49

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 70.6 | 45.6 | 45.6 | 45.6 | 36.2 | 70.9 | 46.4 |
| Propane | 5.0 | 29.4 | 54.4 | 54.4 | 54.4 | 63.8 | 29.1 | 53.6 |
| Composition (lb/h) | | | | | | | | |
| Propylene | 18,955 | 28,283 | 9,899 | 990 | 8,909 | 570 | 419 | 9,329 |
| Propane | 1,045 | 12,345 | 12,354 | 1,235 | 11,119 | 1,055 | 181 | 11,300 |

Membrane Area = 200 m$^2$
Theoretical Compressor hp = 18 hp

Example 57

TABLE 50

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 65.6 | 40.0 | 40.0 | 40.0 | 20.0 | 59.9 | 41.0 |
| Propane | 5.0 | 34.4 | 60.0 | 60.0 | 60.0 | 80.0 | 40.1 | 59.0 |
| Composition (lb/h) | | | | | | | | |
| Propylene | 18,955 | 28,772 | 10,070 | 1,007 | 9,063 | 252 | 755 | 9,818 |
| Propane | 1,045 | 15,833 | 15,843 | 1,584 | 14,258 | 1,055 | 529 | 14,787 |

Membrane Area = 500 m$^2$
Theoretical Compressor hp = 39 hp

Example 58

TABLE 51

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 57.5 | 32.2 | 32.2 | 32.2 | 7.4 | 44.8 | 33.0 |
| Propane | 5.0 | 42.5 | 67.8 | 67.8 | 67.8 | 92.6 | 55.2 | 67.0 |
| Composition (lb/h) | | | | | | | | |
| Propylene | 18,955 | 29,038 | 10,164 | 1,016 | 9,147 | 79.7 | 937 | 10,084 |
| Propane | 1,045 | 22,481 | 22,476 | 2,248 | 20,228 | 1,040 | 1,208 | 21,436 |

Membrane Area = 1,000 m$^2$
Theoretical Compressor hp = 64 hp

Example 59

The results of Examples 51 and 56–58 are compiled in Table 52.

TABLE 52

| Exp. # | Membrane Area (m$^2$) | Theoretical Compressor HP | Propylene vented (lost) (lb/h) (Stream 916) | Propylene concentration (%) (Stream 916) | Propylene recovered (lb/h) (Stream 917) | Propane in reactor feed (%) (Stream 904) |
|---|---|---|---|---|---|---|
| 51 | 0 | — | 968 | 49.0 | — | 26.6 |
| 56 | 200 | 18 | 570 | 36.2 | 419 | 29.4 |
| 57 | 500 | 39 | 252 | 20.0 | 755 | 34.4 |
| 58 | 1,000 | 64 | 79.7 | 7.4 | 937 | 42.5 |

Set 2. Examples 60–63
Process of the Invention; 20% of Overhead Treated by Membrane The calculations of Examples 56–59 were repeated, the only difference being that 20% of overhead stream 913 was sent as stream 914 for treatment in the membrane separation step. The results are shown in Tables 53–55 and compiled in Table 56.

Example 60

TABLE 53

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 83.0 | 63.1 | 63.1 | 63.1 | 56.1 | 84.2 | 64.4 |
| Propane | 5.0 | 17.0 | 36.9 | 36.9 | 36.9 | 43.9 | 15.8 | 35.6 |
| Composition (lb/h) | | | | | | | | |
| Propylene | 18,955 | 27,206 | 9,522 | 1,904 | 7,618 | 1,271 | 634 | 8,252 |
| Propane | 1,045 | 5,833 | 5,829 | 1,166 | 4,663 | 1,041 | 125 | 4,787 |

Membrane Area = 200 m$^2$
Theoretical Compressor hp = 24 hp

Example 61

TABLE 54

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 80.6 | 59.2 | 59.2 | 59.2 | 39.7 | 78.3 | 61.4 |
| Propane | 5.0 | 19.4 | 40.8 | 40.8 | 40.8 | 60.3 | 21.7 | 38.6 |
| Composition (lb/h) | | | | | | | | |
| Propylene | 18,955 | 28,156 | 9,855 | 1,971 | 7,884 | 654 | 1,317 | 9,201 |
| Propane | 1,045 | 7,116 | 7,112 | 1,422 | 5,689 | 1,041 | 381 | 6,071 |

Membrane Area = 500 m$^2$
Theoretical Compressor hp = 52 hp

Example 62

TABLE 55

| Stream | 901 | 904 | 913 | 914 | 915 | 916 | 917 | 918 |
|---|---|---|---|---|---|---|---|---|
| Composition (mol %) | | | | | | | | |
| Proplene | 95.0 | 74.9 | 51.1 | 51.1 | 51.1 | 17.3 | 66.0 | 53.3 |
| Propane | 5.0 | 25.1 | 48.9 | 48.9 | 48.9 | 82.7 | 34.0 | 46.7 |
| Composition (lb/h) | | | | | | | | |
| Propylene | 18,955 | 28,841 | 10,094 | 2,019 | 8,076 | 208 | 1,811 | 9,886 |
| Propane | 1,045 | 10,110 | 10,107 | 2,021 | 8,085 | 1,043 | 979 | 9,064 |

Membrane Area = 1,000 m$^2$
Theoretical Compressor hp = 64 hp

Example 63

The results of Examples 52 and 60–62 are compiled in Table 56.

TABLE 56

| Exp. # | Membrane Area (m$^2$) | Theoretical Compressor HP | Propylene vented (lost) (lb/h) (Stream 916) | Propylene concentration (%) (Stream 916) | Propylene recovered (lb/h) (Stream 917) | Propane in reactor feed (%) (Stream 904) |
|---|---|---|---|---|---|---|
| 52 | 0 | — | 1,843 | 65.0 | — | 15.9 |
| 60 | 200 | 24 | 1,271 | 56.1 | 634 | 17.0 |

TABLE 56-continued

| Exp. # | Membrane Area (m²) | Theoretical Compressor HP | Propylene vented (lost) (lb/h) (Stream 916) | Propylene concentration (%) (Stream 916) | Propylene recovered (lb/h) (Stream 917) | Propane in reactor feed (%) (Stream 904) |
|---|---|---|---|---|---|---|
| 61 | 500 | 52 | 654 | 39.7 | 1,317 | 19.4 |
| 62 | 1,000 | 84 | 208 | 17.3 | 1,811 | 25.1 |

Set 2. Examples 64–67
Process of the Invention; 30% of Overhead tream Treated by Membrane The calculations of Examples 56–59 were repeated, the only difference being that 30% of overhead stream 913 was sent as stream 914 for treatment in the membrane separation step. The results are shown in Tables 57–59 and compiled in Table 60.

Example 64

TABLE 57

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 87.8 | 71.6 | 71.6 | 71.6 | 66.7 | 89.1 | 73.1 |
| Propane | 5.0 | 12.2 | 28.4 | 28.4 | 28.4 | 33.3 | 10.9 | 26.9 |
| Composition (lb/h) | | | | | | | | |
| Propylene | 18,955 | 26,092 | 9,132 | 2,740 | 6,393 | 1,995 | 744 | 7,137 |
| Propane | 1,045 | 3,798 | 3,796 | 1,139 | 2,657 | 1,043 | 95.6 | 2,753 |

Membrane Area = 200 m²
Theoretical Compressor hp = 26 hp

Example 65

TABLE 58

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 86.6 | 69.3 | 69.3 | 69.3 | 54.6 | 85.9 | 72.1 |
| Propane | 5.0 | 13.4 | 30.7 | 30.7 | 30.7 | 45.4 | 14.1 | 27.9 |
| Composition (lb/h) | | | | | | | | |
| Propylene | 18,955 | 27,323 | 9,563 | 2,869 | 6,694 | 1,195 | 1,674 | 8,368 |
| Propane | 1,045 | 4,439 | 4,437 | 1,331 | 3,106 | 1,043 | 288 | 3,394 |

Membrane Area = 500 m²
Theoretical Compressor hp = 60 hp

Example 66

TABLE 59

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 83.1 | 63.2 | 63.2 | 63.2 | 29.7 | 77.6 | 66.6 |
| Propane | 5.0 | 16.9 | 36.8 | 36.8 | 36.8 | 70.3 | 22.4 | 33.4 |
| Composition (lb/h) | | | | | | | | |
| Propylene | 18,955 | 28,514 | 9,980 | 2,994 | 6,986 | 421 | 2,573 | 9,559 |
| Propane | 1,045 | 6,079 | 6,077 | 1,823 | 4,254 | 1,044 | 779 | 5,033 |

Membrane Area = 1,000 m²
Theoretical Compressor hp = 101 hp

Example 67

The results of Examples 53 and 64–66 are compiled in Table 60.

TABLE 60

| Exp. # | Membrane Area ($m^2$) | Theoretical Compressor HP | Propylene vented (lost) (lb/h) (Stream 916) | Propylene concentration (%) (Stream 916) | Propylene recovered (lb/h) (Stream 917) | Propane in reactor feed (%) (Stream 904) |
|---|---|---|---|---|---|---|
| 53 | 0 | — | 2,636 | 72.5 | — | 11.7 |
| 64 | 200 | 26 | 1,995 | 66.7 | 744 | 12.2 |
| 65 | 500 | 60 | 1,195 | 54.6 | 1,674 | 13.4 |
| 66 | 1,000 | 101 | 421 | 29.7 | 2,573 | 16.9 |

Set 2. Examples 68–71
Process of the Invention; 40% of Overhead Treated by Membrane The calculations of Examples 56–59 were repeated, the only difference being that 40% of overhead stream 913 was sent as stream 914 for treatment in the membrane separation step. The results are shown in Tables 61–63 and compiled in Table 64.

Example 68

TABLE 61

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 90.3 | 76.6 | 76.6 | 76.6 | 73.0 | 91.6 | 78.3 |
| Propane | 5.0 | 9.7 | 23.4 | 23.4 | 23.4 | 27.0 | 8.4 | 21.7 |
| Composition (lb/h) | | | | | | | | |
| Propylene | 18,955 | 25,019 | 8,757 | 3,503 | 5,254 | 2,692 | 810 | 6,064 |
| Propane | 1,045 | 2,807 | 2,805 | 1,122 | 1,683 | 1,044 | 78.4 | 1,762 |

Membrane Area = 200 $m^2$
Theoretical Compressor hp = 28 hp

Example 69

TABLE 62

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 89.7 | 75.3 | 75.3 | 75.3 | 64.4 | 89.6 | 78.5 |
| Propane | 5.0 | 10.3 | 24.7 | 24.7 | 24.7 | 35.6 | 10.4 | 21.5 |

TABLE 62-continued

| Stream | 901 | 904 | 913 | 914 | 915 | 916 | 917 | 918 |
|---|---|---|---|---|---|---|---|---|
| Composition (lb/h) | | | | | | | | |
| Propylene | 18,955 | 26,395 | 9,238 | 3,695 | 5,543 | 1,798 | 1,897 | 7,440 |
| Propane | 1,045 | 3,185 | 3,183 | 1,273 | 1,910 | 1,044 | 230 | 2,140 |

Membrane Area = 500 $m^2$
Theoretical Compressor hp = 66 hp

Example 70

TABLE 63

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 87.6 | 71.2 | 71.2 | 71.2 | 42.7 | 84.3 | 75.3 |
| Propane | 5.0 | 12.4 | 28.8 | 28.8 | 28.8 | 57.3 | 15.7 | 24.7 |
| Composition (lb/h) | | | | | | | | |
| Propylene | 18,955 | 28,021 | 9,808 | 3,923 | 5,885 | 741 | 3,182 | 9,067 |
| Propane | 1,045 | 4,160 | 4,158 | 1,663 | 2,495 | 1,044 | 620 | 3,115 |

Membrane Area = 1,000 $m^2$
Theoretical Compressor hp = 115 hp

Example 71

The results of Examples 54 and 68–70 are compiled in Table 64.

TABLE 64

| Exp. # | Membrane Area ($m^2$) | Theoretical Compressor HP | Propylene vented (lost) (lb/h) (Stream 916) | Propylene concentration (%) (Stream 916) | Propylene recovered (lb/h) (Stream 917) | Propane in reactor feed (%) (Stream 904) |
|---|---|---|---|---|---|---|
| 54 | 0 | — | 3,359 | 77.1 | — | 9.4 |
| 68 | 200 | 28 | 2,692 | 73.0 | 810 | 9.7 |
| 69 | 500 | 66 | 1,798 | 64.4 | 1,897 | 10.3 |
| 70 | 1,000 | 115 | 741 | 42.7 | 3,182 | 12.4 |

The tables show how the use of a membrane separation step can cut the propylene loss in relation to propane vented enormously, as compared with the prior art cases. The flexibility of the process to meet specific goals is also highlighted. For example, if the primary consideration is to keep the propane concentration in the reactor feed, and hence in the reactor, to a low level, this is best achieved by sending a high proportion of the overhead gas, such as 40%, through the membrane treatment path as stream 914. Simultaneously, the propylene loss can be held to a very low level, such as only 740 lb/h, by using a relatively large membrane area (1,000 m$^2$).

Set 3. Examples 72–75
Fixed Propylene/Propane Vent Stream

A set of computer calculations was performed to model the process of the invention according to the design of FIG. 9, including the membrane system. The process parameters were set to match the vent stream of Example 52, that is, propylene loss of about 1,842 lb/h and propane loss of about 1,045 lb/h.

The split of stream 913 between streams 914 and 915 was varied from 30:70 (30% sent to membrane treatment) to 50:50. The results of the calculations are shown in Tables 65–67 and compiled in Table 68. Stream numbers refer to FIG. 9.

Example 72
(Stream 914 30% of Overhead)

TABLE 65

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 87.6 | 71.3 | 71.3 | 71.3 | 65.0 | 88.7 | 73.0 |
| Propane | 5.0 | 12.4 | 28.7 | 28.7 | 28.7 | 35.0 | 11.3 | 27.0 |
| Composition (lb/h) | | | | | | | | |
| Propylene | 18,955 | 26,312 | 9,210 | 2,763 | 6,447 | 1,852 | 910 | 7,357 |
| Propane | 1,045 | 3,890 | 3,890 | 1,167 | 2,723 | 1,045 | 122 | 2,845 |

Membrane Area = 248 m$^2$
Theoretical Compressor hp = 32 hp

Example 73
(Stream 914 40% of Overhead)

TABLE 66

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 89.7 | 75.3 | 75.3 | 75.3 | 65.0 | 89.8 | 78.5 |
| Propane | 5.0 | 10.3 | 24.7 | 24.7 | 24.7 | 35.0 | 10.2 | 21.5 |
| Composition (lb/h) | | | | | | | | |
| Propylene | 18,955 | 26,309 | 9,208 | 3,683 | 5,525 | 1,853 | 1,830 | 7,354 |
| Propane | 1,045 | 3,157 | 3,157 | 1,263 | 1,894 | 1,045 | 217 | 2,111 |

Membrane Area = 479 m$^2$
Theoretical Compressor hp = 63 hp

Example 74
(Stream 914 50% of Overhead)

TABLE 67

| Stream | 901 | 904 | 913 | 914 | 915 | 916 | 917 | 918 |
|---|---|---|---|---|---|---|---|---|
| Composition (mol %) | | | | | | | | |
| Propylene | 95.0 | 91.1 | 78.2 | 78.2 | 78.2 | 65.0 | 90.6 | 82.4 |
| Propane | 5.0 | 8.9 | 21.8 | 21.8 | 21.8 | 35.0 | 9.4 | 17.6 |
| Composition (lb/h) | | | | | | | | |
| Propylene | 18,955 | 26,306 | 9,206 | 4,603 | 4,603 | 1,854 | 2,748 | 7,351 |
| Propane | 1,045 | 2,686 | 2,687 | 1,343 | 1,343 | 1,046 | 298 | 1,641 |

Membrane Area = 700 m$^2$
Theoretical Compressor hp = 94 hp

Example 75

The results of Examples 52 and 72–74 are compiled in Table 68.

TABLE 68

| Exp. # | Split ratio (recycle/purge) (%) | Membrane Area (m$^2$) | Theoretical Compressor HP | Propane in reactor off-gas (%) (Stream 913) | Propane in reactor feed (%) (Stream 904) |
|---|---|---|---|---|---|
| 52 | 80/20 | — | — | 35.1 | 15.9 |
| 72 | 70/30 | 248 | 32 | 28.7 | 12.4 |
| 73 | 60/40 | 479 | 63 | 24.7 | 10.3 |
| 74 | 50/50 | 700 | 94 | 21.8 | 8.9 |

As can be seen clearly from Table 68, the presence of the membrane separation step alters trade-off between propylene loss and reactor feed composition substantially. In each case, the propylene loss, 1,842 lb/h, is contained at a level the same as that achieved in the "no membrane" case that relied on 80% direct recycle. However, while the propylene loss is thus contained, the concentration of propane in the reactor feed stream is driven down from 15.9% in the "no membrane" case, to only 8.9% in the case in which 50% of the purge gas is subjected to the membrane separation treatment.

GROUP V EXAMPLES

N-butanol

Figure 10:
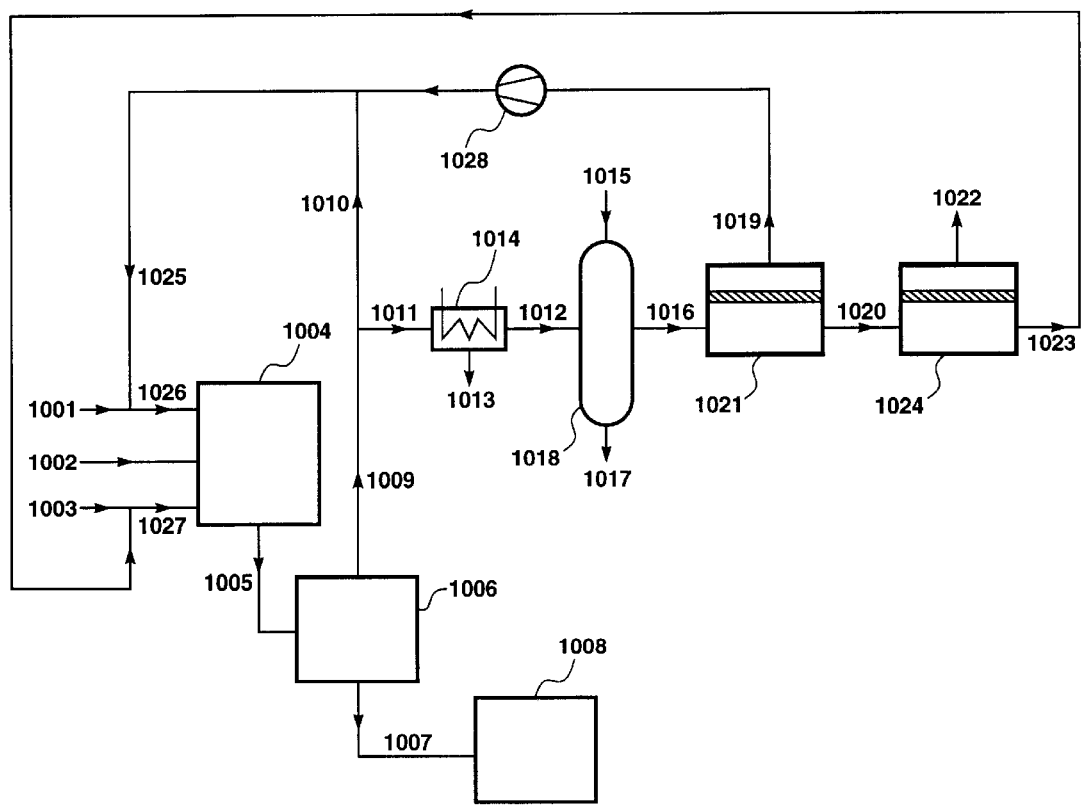
FIG. 10 is a schematic drawing of an n-butanol production process according to the invention.

In a typical n-butanol manufacturing process by catalytic hydroformylation, a multi-staged process as depicted in FIG. 10 is used. Propylene, stream 1001, hydrogen, stream 1002, and carbon monoxide, stream 1003, are passed into a first reactor or set of reactors 1004. A dissolved catalyst stream, not shown for simplicity, is also passed into the reactor. Various oxo reactions take place, resulting in the formation of a mixture of several normal and iso aldehydes and alcohols. The reactor effluent, stream 1005, is passed to a separation step or series of steps, 1006, where catalyst is recovered for return to the reactor, and where crude butyraldehyde solution, stream 1007, is separated from other components. Alcohol production is completed by passing the butyraldehyde to downstream hydrogenation in a second reactor or series of reactors and to purification, these steps being indicated overall as box 1008, to yield the finished n-butanol product.

Methane, propane and carbon dioxide enter the primary reactor as impurities with the syn gas and propylene feeds. Additional carbon dioxide is generated by side reactions in the process. The combination of these gases reduces reactor productivity as for the other manufacturing processes discussed above, but in particular, high levels of carbon dioxide have the potential for severe catalyst damage by poisoning.

The light overhead gas stream, 1009, containing these impurities, as well as butyraldehyde, unreacted propylene and other feedstock, is withdrawn from the separator section. Part of stream 1009 is recirculated as stream 1010 and 1025 to the reactor inlet, where it is mixed with the incoming propylene stream to form reactor feed stream 1026. A portion of stream 1009 is purged from the reactor loop as stream 1011 to control build-up of the inerts such as propane, methane and carbon dioxide in the reactor.

Two computer modeling calculations were run based on this exemplary process configuration. Only the calculations for the section of the process relating to treatment of the overhead gases from the separator section are shown.

The first calculation was performed to simulate a prior art process, assuming that a portion of stream 1009 is simply vented from the process as stream 1011.

The second calculation was performed according to the process of the invention including the following steps: (i) condensation to recover butyraldehyde, (ii) amine scrubbing to remove carbon dioxide, (iii) membrane separation to separate propylene from propane, and (iv) membrane separation to separate hydrocarbons from carbon monoxide.

Example 76
Not in Accordance with the Invention

Table 69 shows the composition of the vented portion, stream 1011, of an overhead gas stream from a typical average-size butyraldehyde reactor. The vent stream total flow rate is about 250 scfm.

TABLE 69

| Stream 1011 | Composition (mol %) | Composition (lb/h) |
|---|---|---|
| n-Butyraldehyde | 8.0 | 241 |
| Propylene | 28.1 | 492 |
| Hydrogen | 17.7 | 15 |
| Carbon Monoxide | 19.1 | 222 |

TABLE 69-continued

| Stream 1011 | Composition (mol %) | Composition (lb/h) |
|---|---|---|
| Carbon Dioxide | 6.0 | 110 |
| Methane | 8.0 | 54 |
| Propane | 13.0 | 239 |
| Total Flow | 100.0 | 1,373 |

In a real prior art process, this gas removed from the reactor loop is typically sent to the plant fuel header.

Example 77

Process of the Invention

A computer calculation was performed to model the process of the invention according to the design of FIG. 10. As shown in FIG. 10, stream 1011 was assumed to be passed to a condensation step, 1014, to recover additional butyraldehyde as stream 1013. The remaining uncondensed gas, stream 1012, was assumed to be sent to an amine or caustic scrubber, unit 1018, where a scrubbing agent (for example, sodium hydroxide), stream 1015, is used to remove carbon dioxide, as waste stream 1017. The scrubbed carbon-dioxide-depleted stream, 1016, was assumed to be sent to the first membrane separation step, 1021, containing membranes selective for propylene over propane. Propylene-enriched permeate stream 1019 was assumed to be recompressed in compressor 1028, mixed with recycle stream 1010, recycled to the reactor via line 1025, and mixed with propylene feed stream 1001 to form reactor feed stream 1026. The propylene-depleted residue stream, 1020, was assumed to be fed to a second membrane separation step, 1024, containing membranes selective for the hydrocarbon components of the stream, primarily propane and methane, over carbon monoxide. The hydrocarbon-enriched permeate stream, 1022, is discharged from the process. The carbon-monoxide-enriched residue stream, 1023, was assumed to be recycled to the reactor and mixed with carbon monoxide feed stream 1003 to form stream 1027 to the reactor. Any portion of off-gas stream 1009 that was not passed to the condensation/scrubber/membrane treatment train was assumed to be recirculated directly to the reactor via lines 1010 and 1025.

The calculation was run so as to vent about the same amount of propane, about 240 lb/h, from the process as in the prior art calculation above. The results of the calculations are shown in Table 70. Because of the addition of recycle streams 1019 and 1023 to the reactor, the total flow rate of overhead gas stream 1009 is larger than in "no-treatment" Example 76. Consequently, the portion of stream 1009 that is purged as stream 1011 is correspondingly larger, and totals approximately 418 scfm. Stream numbers refer to FIG. 10.

TABLE 70

| Stream | 1011 | 1012 | 1013 | 1016 | 1017 | 1019 | 1020 | 1022 | 1023 |
|---|---|---|---|---|---|---|---|---|---|
| Composition (mol %) | | | | | | | | | |
| n-Butyraldehyde | 8.0 | 0.6 | 56.4 | 0.7 | 0.0 | 0.3 | 1.3 | 1.7 | — |
| Propylene | 28.1 | 27.9 | 29.6 | 29.8 | 0.0 | 35.7 | 19.7 | 25.5 | 1.3 |
| Hydrogen | 17.7 | 20.5 | 0.0 | 21.8 | 0.0 | 34.1 | 1.2 | 1.2 | 1.1 |
| Carbon Monoxide | 19.1 | 22.0 | 0.0 | 23.4 | 0.0 | 17.1 | 34.1 | 22.5 | 70.7 |
| Carbon Dioxide | 6.0 | 6.6 | 1.7 | 0.4 | 100.0 | 0.5 | — | 0.1 | — |
| Methane | 8.0 | 9.3 | 0.0 | 9.9 | 0.0 | 6.2 | 16.1 | 14.0 | 22.7 |
| Propane | 13.0 | 13.2 | 12.1 | 14.1 | 0.0 | 6.1 | 27.5 | 34.9 | 4.1 |
| Composition (lb/h) | | | | | | | | | |
| n-Butyraldehyde | 405 | 27.4 | 378 | 27.4 | 0 | 7.5 | 20.0 | 19.8 | 0.2 |
| Propylene | 827 | 711 | 116 | 711 | 0 | 536 | 175 | 172 | 2.8 |
| Hydrogen | 25.0 | 25.0 | — | 25.0 | 0 | 24.5 | 0.5 | 0.4 | 0.1 |
| Carbon Monoxide | 373 | 373 | — | 373 | 0 | 171 | 202 | 101 | 100 |
| Carbon Dioxide | 185 | 177 | 8.0 | 8.8 | 168 | 8.1 | 0.8 | 0.7 | — |
| Methane | 90.0 | 90.0 | — | 90.0 | 0 | 35.3 | 54.7 | 36.2 | 18.5 |
| Propane | 402 | 352 | 49.5 | 352 | 0 | 95.9 | 257 | 247 | 9.1 |

— = less than 0.1
Membrane Area = 500 m$^2$ (300 m$^2$ in unit 1021 + 200 m$^2$ in unit 1024)
Theoretical Compressor hp = 42 hp The total flow rate of vent stream 1022 is 578 lb/h, a nearly 60% reduction compared to the prior art vent gas flow rate of 1,373 lb/h. The propylene loss in the vented gas is cut from 492 lb/h to 172 lb/h. In addition to the many other advantages provided by the process of the invention, the reduction in flow rate of vent gas to the fuel header may aid in debottlenecking in plants where fuel gas generation is at capacity, thereby allowing throughput of the unit operations generating the overhead gas to be increased.

Example 78

Table 71 shows the improved product and feedstock recovery achieved by the process of the invention compared to the prior art no-treatment process.

| Composition | Prior art vent stream 1011 | Current vent streams 1022/1017 | Recovered/ recycled compared to prior art | Improvement in current vent |
|---|---|---|---|---|
| | Stream flow (lb/h) | | | |
| n-Butyraldehyde | 241 | 19.8 | 221 | — |
| Propylene | 492 | 172 | 320 | — |
| Hydrogen | 15.0 | 0.4 | 15.0 | — |
| Carbon Monoxide | 222 | 101 | 121 | — |
| Carbon Dioxide | 110 | 168 | — | 58 |
| Methane | 54.0 | 36.2 | — | (18) |
| Propane | 239 | 247 | — | 8 |

As can be seen, more than 90% of the crude butyraldehyde product that was lost in the prior art vent stream is recovered as stream 1013 with the process of the invention. Approximately two-thirds of the propylene feedstock that was lost in the prior art vent stream is recovered as stream 1019 with the process of the invention. More than half the carbon monoxide in the synthesis gas feedstock that was lost in the prior art vent stream is recovered as stream 1023 with the process of the invention. At the same time, there is a 50% increase in the removal of carbon dioxide from the reactor loop, and approximately the same amount of propane is vented from the reactor loop as in the prior art vent.

We claim:

1. A process for producing isopropyl alcohol, comprising the steps of:

(a) carrying out the reaction of propylene with water in a reaction zone;

(b) withdrawing from the reaction zone an effluent comprising propylene, propane and isopropyl alcohol;

(c) subjecting the effluent to at least one separation step, thereby producing a raw isopropyl alcohol stream and a gas stream;

(d) passing at least a portion of the gas stream across a feed side of a membrane selective for propylene over propane;

(e) withdrawing from a permeate side of the membrane a permeate stream enriched in propylene compared to the gas stream, but having a propylene concentration that is lower than about 95%;

(f) withdrawing from the feed side a residue stream enriched in propane compared to the gas stream;

(g) recirculating at least a portion of the permeate stream to the reaction zone.

2. The process of claim 1, wherein the permeate stream has a propylene concentration that is lower than about 95%.

3. The process of claim 1, wherein the residue stream has a propane concentration of at least about 30%.

4. The process of claim 1, wherein the permeate stream is enriched in propylene compared with the gas stream by no more than about 10%.

5. The process of claim 1, wherein the residue stream is enriched in propane compared with the gas stream by at least about 10%.

6. The process of claim 1, wherein the separation step comprises flash evaporation.

7. The process of claim 1, wherein the separation step comprises cooling and condensation.

8. The process of claim 1, wherein the separation step comprises distillation.

9. The process of claim 1, wherein the membrane is a polymeric membrane.

10. The process of claim 9, wherein the polymeric membrane comprises a selective layer comprising a polymer chosen from the group consisting of polyimides, poly (phenylene oxides), perfluorinated dioxoles, perfluorinated dioxolanes and perfluorinated cyclic ethers.

11. The process of claim 1, wherein the membrane exhibits a selectivity for propylene over propane, when in use in the process, of at least about 2.

12. The process of claim 1, wherein the membrane exhibits a selectivity for propylene over propane, when in use in the process, of at least about 3.

13. The process of claim 1, wherein only a portion of the gas stream is subjected to step (d) and another portion of the gas stream is recirculated to the reaction zone without being subjected to step (d).

14. The process of claim 1, wherein all of the gas stream is subjected to step (d).

15. The process of claim 1, wherein the residue stream is enriched in propane compared with the gas stream by at least about 10%.

16. The process of claim 1, wherein the residue stream has a propane concentration of at least about 15%.

* * * * *